(12) United States Patent
Favilli et al.

(10) Patent No.: US 9,550,133 B2
(45) Date of Patent: Jan. 24, 2017

(54) PROCESS AND EQUIPMENT FOR SEPARATING 1,2,4 TRIMETHYLBENZENE (PSEUDOCUMENE) FROM A MIXTURE CONTAINING AROMATIC HYDROCARBONS

(75) Inventors: Stefano Favilli, Rosignano Marittimo (IT); Luciano Scibola, Crema (IT)

(73) Assignee: SIME SRL, Rosignano Solvay (LI) (IT)

( * ) Notice: Subject to any disclaimer, the term of this patent is extended or adjusted under 35 U.S.C. 154(b) by 420 days.

(21) Appl. No.: 13/878,813

(22) PCT Filed: Oct. 11, 2011

(86) PCT No.: PCT/IB2011/002388
§ 371 (c)(1),
(2), (4) Date: Jun. 19, 2013

(87) PCT Pub. No.: WO2012/056278
PCT Pub. Date: May 3, 2012

(65) Prior Publication Data
US 2013/0267751 A1    Oct. 10, 2013

(30) Foreign Application Priority Data
Oct. 11, 2010 (IT) .................. PI2010A0114

(51) Int. Cl.
| | | |
|---|---|---|
| B01D 3/14 | (2006.01) | |
| B01D 1/28 | (2006.01) | |
| B01D 3/00 | (2006.01) | |
| B01D 3/32 | (2006.01) | |
| C07C 7/04 | (2006.01) | |

(52) U.S. Cl.
CPC . *B01D 3/14* (2013.01); *B01D 1/28* (2013.01); *B01D 3/007* (2013.01); *B01D 3/141* (2013.01); *B01D 3/32* (2013.01); *C07C 7/04* (2013.01)

(58) Field of Classification Search
None
See application file for complete search history.

(56) References Cited

U.S. PATENT DOCUMENTS

| | | | |
|---|---|---|---|
| 2008/0161618 A1 | 7/2008 | Zimmermann et al. | |
| 2009/0076985 A1* | 3/2009 | Morgan | C11C 3/003 705/500 |
| 2010/0158764 A1* | 6/2010 | Hedrick | C10G 11/18 422/134 |

FOREIGN PATENT DOCUMENTS

| | | |
|---|---|---|
| CN | 1974501 A | 6/2007 |
| CN | 100424055 C | 10/2008 |
| WO | 2010/097318 A1 | 9/2010 |

OTHER PUBLICATIONS

Search Report dated Aug. 27, 2012 for Application No. PCT/IB2011/002388.
Espacenet English abstract of CN 1974501 A.

\* cited by examiner

*Primary Examiner* — Tam M Nguyen
(74) *Attorney, Agent, or Firm* — Ladas & Parry LLP

(57) ABSTRACT

A method and an apparatus (7') for separating 1,2,4-Trimethylbenzene by fractional distillation of a mixture (31) that contains C9 or C9+ aromatic hydrocarbons, and possibly hydrocarbons with less nine nine carbon atoms. In an aspect of the invention, a first distillation step and a second distillation step are carried out in respective distillation chambers (75, 75') defined by a cylindrical vertical container 501 and by an inner partition wall (85) of the container.

23 Claims, 19 Drawing Sheets

Fig. 12B
Fig. 13
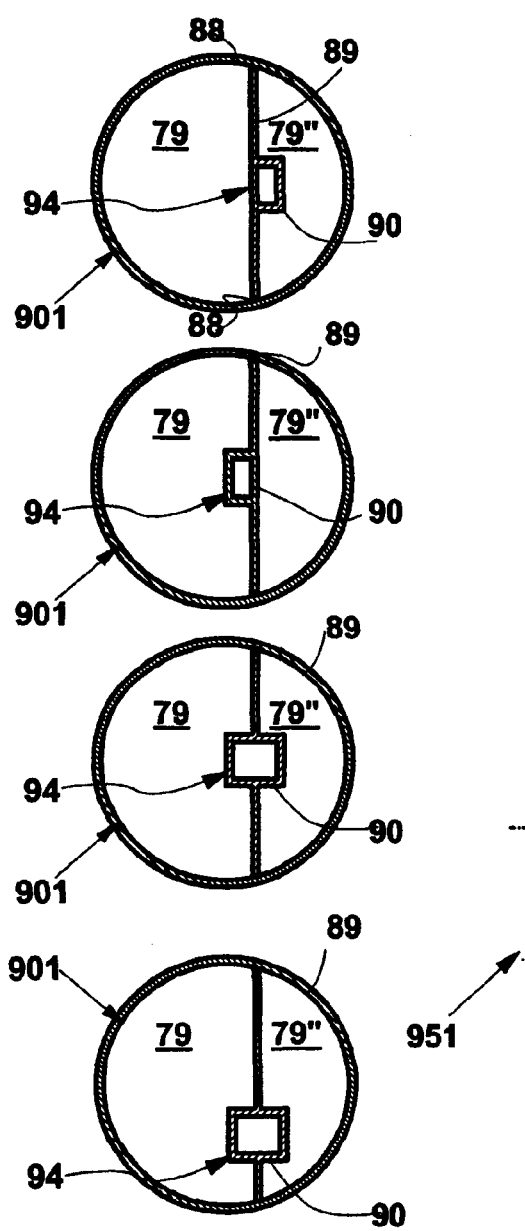
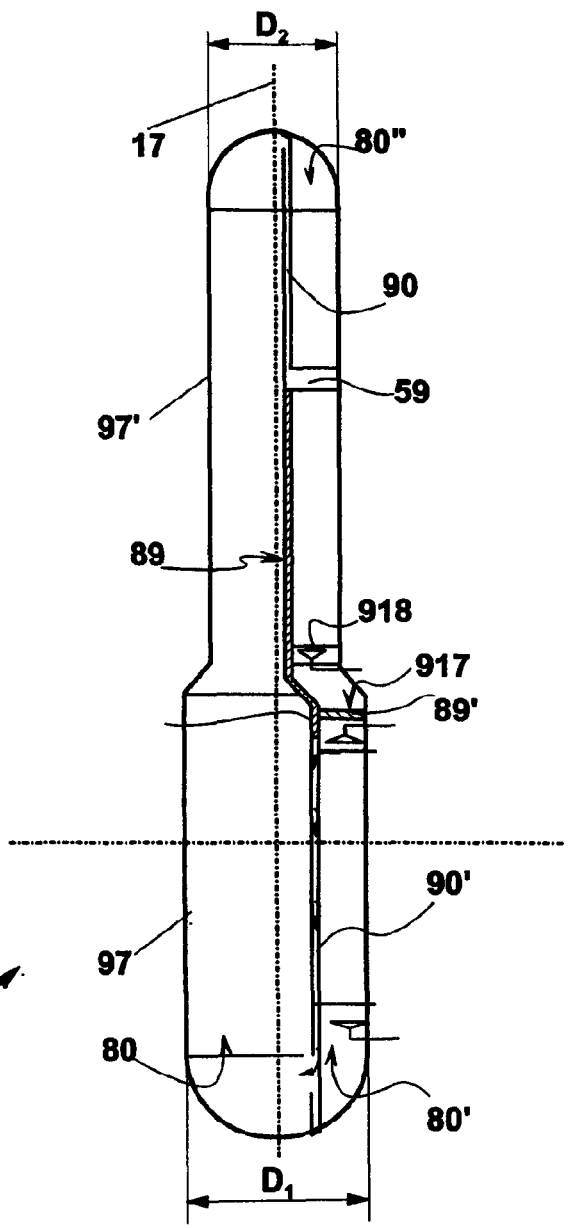

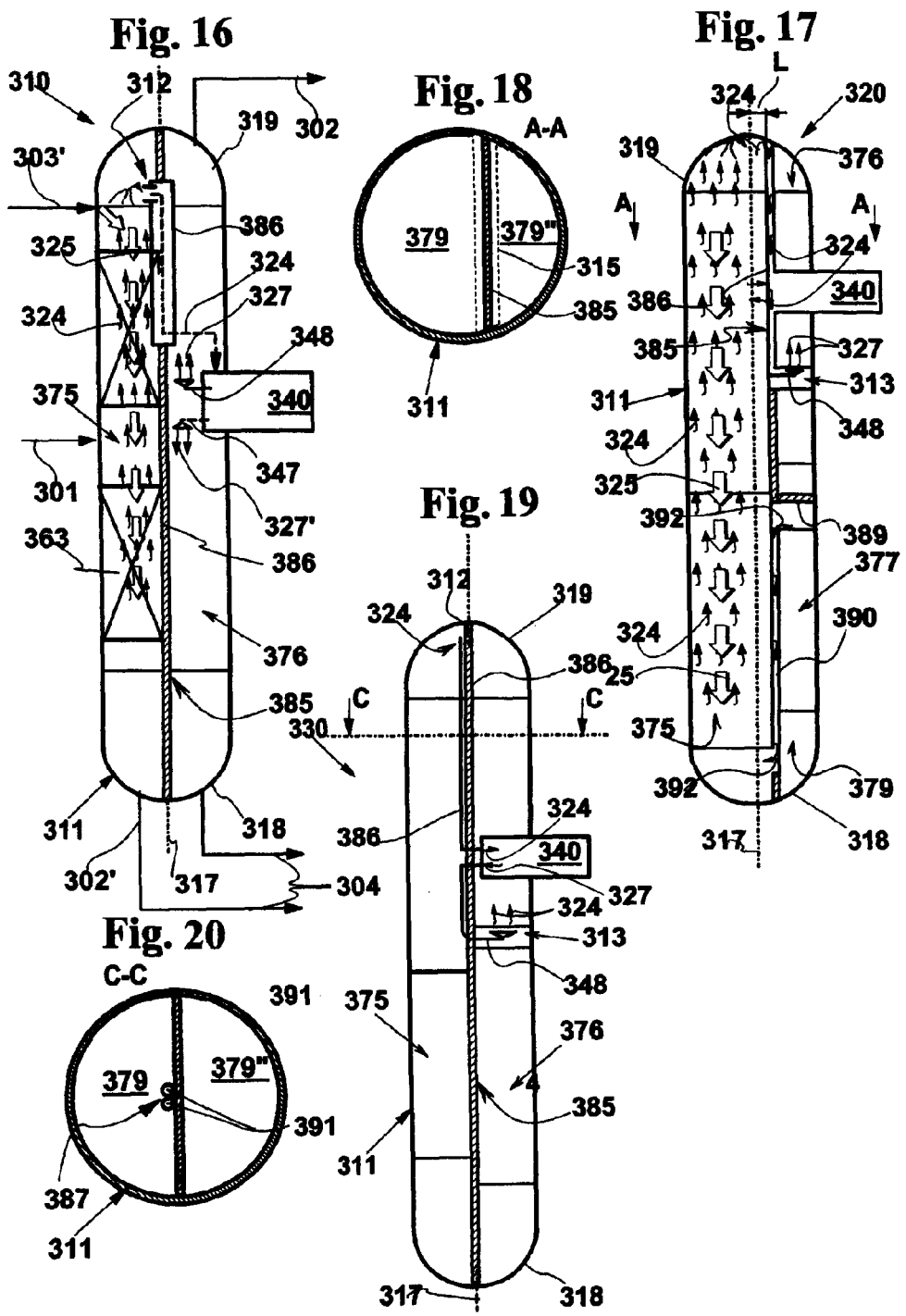

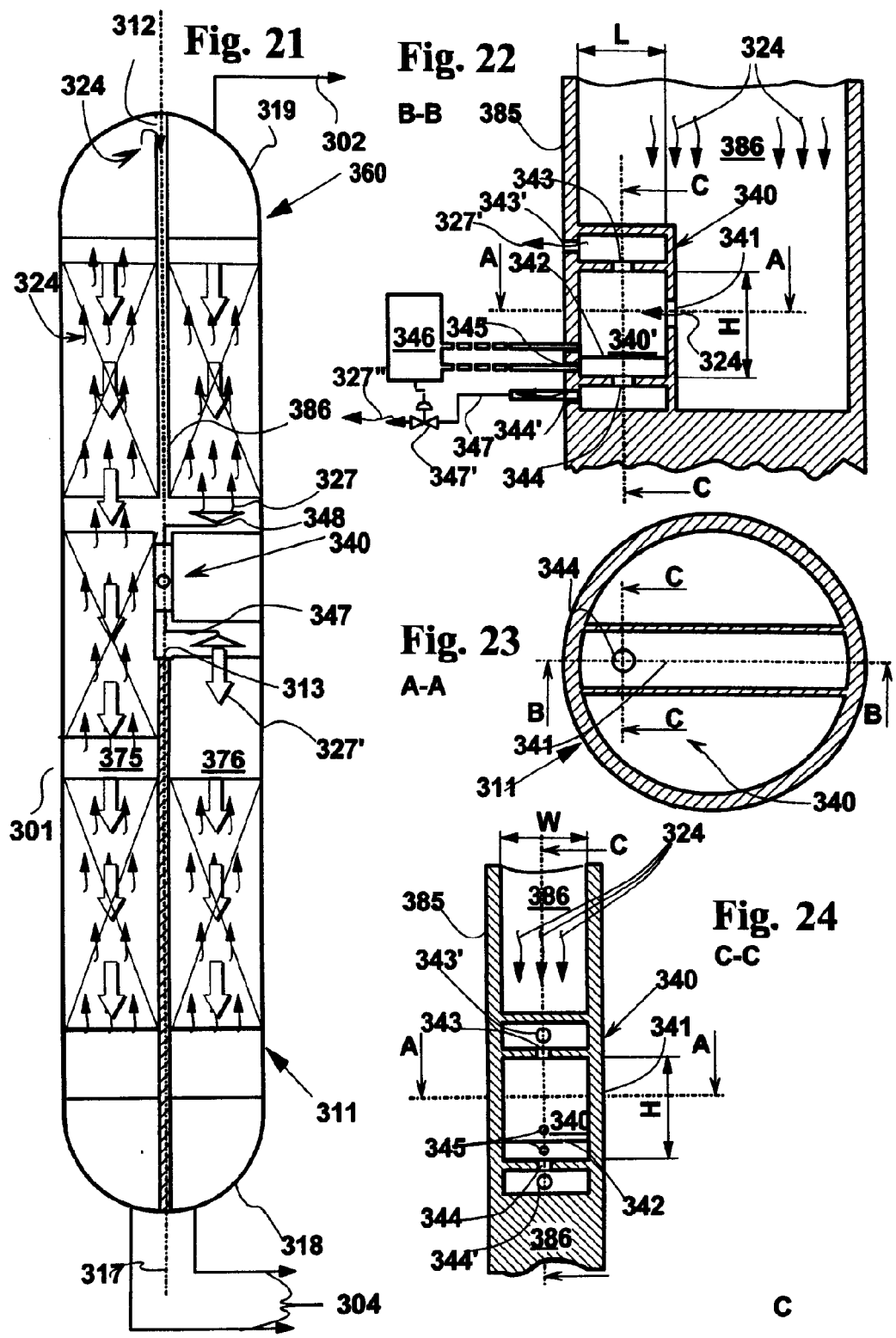

B-B

PROCESS AND EQUIPMENT FOR SEPARATING 1,2,4 TRIMETHYLBENZENE (PSEUDOCUMENE) FROM A MIXTURE CONTAINING AROMATIC HYDROCARBONS

This application is a 371 of PCT/IB2011/002388, filed on Oct. 11, 2011, which claims priority to Italian Patent Application No. PI2010A000114, filed Oct. 11, 2010.

FIELD OF THE INVENTION

The present invention relates to a method and to an apparatus for separating 1,2,4-Trimethylbenzene (Pseudocumene), by fractional distillation, from a mixture containing substantially hydrocarbons with nine carbon atoms (C9) or hydrocarbons with nine and more carbon atoms (C9+). The method and the apparatus allow removing possible minor amounts of hydrocarbons with less than nine carbon atoms.

More in detail, the invention relates to a method and to an apparatus for separating Pseudocumene from a mixture comprising a plurality of hydrocarbons selected among:
  aromatic hydrocarbons that are heavier than Pseudocumene, i.e. aromatic hydrocarbons that have a higher boiling point and/or a relative volatility lower than 1, with respect to Pseudocumene, in particular, 1,2,3-trimethylbenzene (hemimellitene), butylbenzene isomers (sec-, terz-, iso-), methyl isopropyl benzene isomers (cymene, ortho-, meta-, para-), tetramethyl benzenes, benzocyclopentane (indane);
  aromatic hydrocarbons that are lighter than Pseudocumene, in particular, 1,3,5-trimethylbenzene (mesitylene), ethyltoluene isomers (orto-, meta-, para-), isopropylbenzene, n-propylbenzene, but also hydrocarbons that have less than nine carbon atoms, among which olefins, but also C9 olefins that are present in small amount owing to alkylation;
  possible minor amounts of olefins and of paraffins that are heavier and/or lighter than Pseudocumene.

BACKGROUND OF THE INVENTION

Technical Problems

Trialkylated benzenes, in particular, trimethylbenzenes (TMB, isomers 1,2,4-, 1,3,5-, 1,2,3-) are raw material for the industrial production of many important chemical intermediates, in particular oxygen-containing compounds. In particular, 1,2,4-TMB with a suitable purity degree is treated with oxygen in the presence of a catalyst, to obtain Trimellitic Anhydride. Trimellitic Anhydride is largely used as a raw material for making trimellitates, which are high performance plasticizers. Trimellitic Anhydride is widely used for making polyamide-imide coatings, epoxy resins curing agents, cross-linking agents, and for similar uses.

Typically, the TMBs are obtained, as isomer mixtures, from conversion treatments of crude oil distillation fractions such as naphtha, in particular, from catalytic reforming. Such reaction products generally contain other aromatic compounds as well, such as benzene, toluene, xylene.

TMB isomer mixtures can also be obtained by catalytically alkylating aromatic C6-C8 hydrocarbons with methanol.

Isomerization processes of Alkylbenzene mixtures, e.g. TMB are also known.

However, the isomer distribution of industrially obtained TMB mixtures is seldom well suited for a specific application. In other words, it is difficult to achieve a high purity degree of each isomer, in particular, it is difficult to obtain 1,2,4-TMB pure enough to give an acceptable Trimellitic Anhydride yield.

Accordingly, aromatic alkylate separation processes are very important.

At least two distillation steps are required to separate Pseudocumene from such C9 or C9+ mixtures, according to a procedure briefly described hereinafter.

FIG. 1 shows a so-called indirect separation sequence, or "indirect split". In this case, a raw aromatic C9 or C9+ hydrocarbon mixture 11 is fed to a first distillation column 10 from which a bottom fraction 111 and a overhead fraction 13 are obtained. The bottom fraction 111 contains hydrocarbons that are heavier than Pseudocumene, and are substantially free from Pseudocumene. The overhead fraction 13 contains Pseudocumene and lighter aromatic hydrocarbons. The overhead fraction 13 is supplied to the second distillation column 10', from which a overhead fraction 13' lighter than the feed mixture 11, and a bottom fraction 111' of substantially pure Pseudocumene are obtained.

FIG. 2 shows a so-called indirect separation sequence, or "indirect split". In this case, the raw mixture 11 of C9/C9+ aromatic compounds is fed to a first column 10 from which a bottom fraction 121 and a overhead fraction 30 are obtained. The overhead fraction 30 contains hydrocarbons that are lighter than Pseudocumene, and is substantially free from Pseudocumene. The bottom fraction 121 contains Pseudocumene and heavier aromatic hydrocarbons. The bottom fraction 121 is supplied to the second distillation column 10', from which a bottom fraction 121' that is heavier than the fed mixture 11, and a overhead fraction 23' of substantially pure Pseudocumene are obtained. For instance, the method described in CN100424055C is based on this sequence.

In both cases, the columns 10,10' are associated with respective bottom reboilers 20,20'. The reboilers 20',20' may be heated by vapour, by diathermic oil or even by a directly fired heater. A contribute to the heat balance of the first column is given by the feed enthalpy, as well as by the enthalpy of the reflux stream 16 that flows back into the column once the vapour 12 has been condensed. The condensation heat which must be removed in the condensers 14,14' may be transferred to a cooling water stream, otherwise it may be directly dispersed into the environment by an air-cooler equipment. Alternatively, the condensation heat may be recovered for generating low-pressure steam. A part of the condensed overhead vapour 12,12' form a reflux stream 16,16', according to a predetermined reflux ratio. To obtain a substantially quantitative separation of Pseudocumene from lighter/heavier compounds in the first column 10, and from the heavier/lighter compounds in the second column 10' of apparatus 1/2, as well known, a suitable reflux ratio must be used, which is the ratio between the volume of the reflux stream 16,16' and the volume of the distilled stream 13,13', provided that the columns 10,10' have a suitable number of stages.

US 2008161618 describes a process to obtain 1-butene by distillation of a mixture of hydrocarbons with four carbon atoms in a single column comprising two longitudinal chambers that are separated by an inner partition wall. The two chambers serve for corresponding fractional distillation steps, in which the reflux coming from a chamber is used as a feed for the other chamber. Such an apparatus cannot be used to obtain Pseudocumene by consecutive distillation steps of a mixture of aromatic hydrocarbons with nine or more carbon atoms. In fact, such distillation steps are carried out at a temperature remarkably higher than the temperature used for hydrocarbons with four carbon atoms. Typically, the separation of Pseudocumene is carried out at a temperature between 170 and 200° C., in the first distillation, and at a temperature between 160 and 180° C. in the second distillation, whereas temperatures of 30-40° C. and 30-45° C. are used in the case of the 1-butene process. For this reason, in the case of the Pseudocumene process, the temperatures, in particular the temperature difference between the walls of the two longitudinal chambers, would be sensibly higher than the corresponding temperatures and temperature difference of the 1-butene process. Such circumstance is particularly relevant in the steps of start-up and shut-down of the process, in which one of the two chambers may be or may attain the room temperature. In the case of the Pseudocumene process, such temperature differences cause local stresses in the walls of the two chambers that are much higher, in particular, in the inner partition wall and in the joints between the inner partition wall and the body of the column, which the column of US 2008016161 could not tolerate without being damaged. In particular, the stability of the temperatures and of the connections could be seriously impaired when starting up and shutting down the process, for a planned maintenance operation or in an emergency circumstance.

However, the boiling points of Pseudocumene and of some aromatic hydrocarbons that are contained in the raw mixture are very close to one another, and the relative volatilities of the various components are close to 1. A reference, industrially acceptable Pseudocumene purity degree value is 98.5%. A reference, industrially acceptable Pseudocumene recovery value is 80%. To obtain such results, according to the diagrams of FIGS. 1 and 2, the following would be required:
  a column of distillation 10,10' with a very high total number of stages, normally set between 250 and 400; very high reflux ratio values, normally set between 15:1 and 30:1. In such super fractionation or super distillation conditions, very large heating and cooling heat amount must be exchanged, and the operating costs would be very high with respect to the value of the separated product. For the same reason, the purchasing costs of the equipment and the construction costs of the fractionation units would be very high, as well as the maintenance costs.

To overcome such drawbacks, processes have also been proposed which provides a chemical modification of the C9 aromatic hydrocarbons to form new compounds which show boiling temperature differences wider than the starting compounds. This way, the rectification separation is much easier. A restoration of at least one of the starting compounds is then provided, once the separation have been carried out. However, such processes comprise further chemical conversion steps, which globally complicate the operation.

Some methods, like the one described in U.S. Pat. No. 5,004,854, provide transalkylation or disproportionation catalytic reactions to obtain Pseudocumene from aromatic hydrocarbon mixtures of various composition. In the case of mixtures produced by reforming of crude oil fractions, such methods have the drawback of requiring, in any case, a preliminary step of distillation, i.e. of prefractionation, for removing aromatic C10+. This globally complicates the process. Furthermore, the typical complications of catalytic reactions processes must be taken into account. In fact, C10+ are a poison or an inhibitor, or respective precursors, for most transalkylation or disproportionation catalysers.

SUMMARY OF THE INVENTION

It is therefore a feature of the present invention to provide a method and an apparatus for separating and recovering Pseudocumene from a mixture of aromatic hydrocarbons with mainly nine carbon atoms by fractional distillation, which allow to limit the investment costs with respect to the methods and apparatus of known type.

It is a feature of the invention to provide such a method and such an apparatus, which allow reducing the cross sectional and height sizes, with respect to the prior art.

It is also a feature of the invention to provide such an apparatus for removing substantially unsaturated hydrocarbons from the hydrocarbon mixture with less needs of space and lower investment costs with respect to of the prior art.

It is also a feature of the invention to provide such an apparatus comprising a column of fractionation with two distinct chambers for performing two consecutive steps of fractionation to obtain Pseudocumene, which is adapted to tolerate without damages a predetermined number of start up and shut down cycles, also in conditions of emergency, of such two consecutive steps. It is also a feature of the invention to provide such an apparatus that is adapted to tolerate in continuous operation without damages the temperature differences typical of such consecutive steps.

It is another feature of the invention to provide such a method and such an apparatus, which allow reducing the energy requirements of the separation of Pseudocumene by distillation, with respect to what possible with the methods and with the apparatus of known type.

These and other objects are achieved by a method, according to an aspect of the invention, for separating and recovering 1,2,4-trimethylbenzene (TMB), i.e. Pseudocumene, from a raw mixture containing, besides 1,2,4trimethylbenzene (TMB), aromatic hydrocarbons with nine carbon atoms and preferably with more than nine carbon atoms, and preferably hydrocarbons with less than nine carbon atoms, in particular, containing at least one compound heavier than 1,2,4-TMB and a compound lighter than 1,2,4-TMB, the method comprising the steps of:
  prearranging a column, i.e. a vertical elongated container, that is provided with an inner partition wall, the container and the inner partition wall defining a first longitudinal chamber and a second longitudinal chamber within the elongated container;
  feeding the raw mixture into the first longitudinal chamber that is maintained within a predetermined first working temperature range and at a predetermined first working pressure;
  extracting a first overhead vapour fraction from the first longitudinal chamber, the first overhead vapour fraction comprising aromatic hydrocarbons that are lighter than Pseudocumene, i.e. aromatic hydrocarbons that have a relative volatility higher than 1, with respect to Pseudocumene;
  extracting a first bottom fraction from the first longitudinal chamber, the first bottom fraction comprising aromatic hydrocarbons that are heavier than Pseudocumene, i.e. aromatic hydrocarbons that have a relative volatility lower than 1, with respect to Pseudocumene;
wherein the first working temperature range and/or the first working pressure are selected in such a way that Pseudocumene is present substantially in only one fraction selected among the first overhead fraction and the first bottom fraction, such that a Pseudocumene-containing fraction and a substantially Pseudocumene-free mixture are extracted from the first longitudinal chamber,
- feeding at least one part of the Pseudocumene-containing fraction into the second longitudinal chamber, the second longitudinal chamber maintained within a predetermined second working temperature range and at a predetermined second working pressure;
- extracting a second overhead vapour fraction from the second longitudinal chamber;
- extracting a second bottom fraction from the second longitudinal chamber;

wherein the second working temperature range and/or the second working pressure are selected in such a way that Pseudocumene is present substantially pure only in one fraction selected among the second overhead fraction and the second bottom fraction, according to whether the amount of the Pseudocumene-containing fraction, which is extracted from the first longitudinal chamber, and supplied to the second longitudinal chamber is at least one part of the first bottom fraction or at least one part of the first overhead fraction, respectively.

This way, the separation of Pseudocumene from the aromatic C9 or C9+ mixture is carried out in a single container, in particular, in a single divided fractionation column, which reduces the overall construction and operating costs of the fractionation unit.

In an exemplary embodiment, indicated as direct sequence, which is suggested by the composition of the raw mixture, the operating temperature range of the first longitudinal chamber is selected in such a way that the Pseudocumene-containing fraction, which is extracted from the first longitudinal chamber, is the bottom fraction, which forms a feed for the second longitudinal chamber for separating Pseudocumene from the compounds heavier than Pseudocumene, whereas the substantially Pseudocumene-free fraction, which is extracted from the first longitudinal chamber, it is the overhead fraction, and the operating temperature range of the second longitudinal chamber, as well as the composition of the feed of the second longitudinal chamber are such that the substantially pure Pseudocumene-containing fraction, which is extracted from the second longitudinal chamber, it is the overhead fraction, which is withdrawn from the fractionation unit as separated Pseudocumene, whereas the substantially Pseudocumene-free fraction, which is extracted from the second longitudinal chamber, is the bottom fraction.

In particular, the operating temperature range of the first longitudinal chamber is set between 160° C. and 210° C., preferably between 160° C. and 195° C., and the working pressure is substantially atmospheric. In a possible solution, the temperatures of the available heating fluids (high-pressure steam) or of the heating fluids that can be generated on site (low-pressure steam) may in some cases allow operation under vacuum in one or both longitudinal chambers.

The raw mixture of aromatic hydrocarbons may come from a reforming treatment, in particular, a catalytic reforming of a crude-oil distillation fraction, in particular, a catalytic reforming of virgin naphtha.

In particular, the concentration of the products lighter than Pseudocumene that are present in the raw mixture is set between 15% and 60% by volume, preferably it is set between 40% and 60% by volume. Such concentration may vary widely; for example, in the case of a C9 mixture coming from a catalytic reforming of a naphtha, the concentration depends upon the process and upon the operating conditions of the reforming, upon the final boiling point of the reformates and, accordingly it depends upon the C9+ cut that is obtained, after a possible removal of C6-C8 hydrocarbons.

In particular, the raw mixture contains less than 10% by volume of 1,2 methylethylbenzene (o-ethyltoluene).

In particular, the raw mixture contains less than 10% by volume of 1,3,5-TMB.

In particular, the raw mixture contains less than 15% by volume of 1,2,3-TMB.

In particular, the overhead fraction is extracted from the first longitudinal chamber at a temperature set between 160° C. and 210° C., preferably between 160° C. and 180° C.

In particular, the bottom fraction is extracted from the first longitudinal chamber at a temperature set between 170° C. and 230° C., preferably between 170° C. and 195° C.

In particular, the concentration of Pseudocumene in the raw mixture is set between il18% and 35% by volume, preferably it is set between 20% and 30% by volume. Also this concentration may range widely, for example, responsive to the process and to the operating conditions of the reforming process which gives the C9 mixture+ that is supplied to the first longitudinal chamber.

In particular, the operating temperature range of the second longitudinal chamber is set between 165° C. and 250° C., preferably between 165° C. and 215° C., and the working pressure of the second longitudinal chamber is preferably the atmospheric pressure.

In particular, the overhead fraction is extracted from the second longitudinal chamber at a temperature set between 165° C. and 210° C., preferably between 165° C. and 185° C.

In particular, the bottom fraction is extracted from the first longitudinal chamber at a temperature set between 180° C. and 250° C., preferably between 185° C. and 215° C.

Alternatively, according to another exemplary embodiment, indicated as indirect sequence, still substantially suggested by the composition of the raw mixture, the operating temperature range of the first longitudinal chamber is selected in such a way that the Pseudocumene-containing product that is extracted from the first longitudinal chamber is the overhead fraction, which forms a feed for the second longitudinal chamber for separating Pseudocumene from the compounds that are lighter than Pseudocumene, whereas the substantially Pseudocumene-free product, which is extracted from the first longitudinal chamber, is the bottom fraction, and the operating temperature range of the second longitudinal chamber, as well as the composition of the feed of the second longitudinal chamber, are such that the Pseudocumene-containing product, which is extracted from the second longitudinal chamber, is the bottom fraction, which is withdrawn from the fractionation unit substantially as pure Pseudocumene, whereas the substantially Pseudocumene-free product, which is extracted from the second longitudinal chamber, is the overhead fraction. In other words, instead of recovering Pseudocumene as a top product of the second longitudinal chamber, it may be recovered as a bottom product.

In particular, the concentration of the products that are heavier than Pseudocumene that are present in the raw mixture is set between 15% and 60% by volume, preferably it is higher than 40% by volume. Different concentration values may also occur, out of the above specified, however by such conditions the same cost advantages cannot be obtained as in case of the above indicated concentrations.

In particular, the operating temperature range of the first longitudinal chamber is set between 165° C. and 250° C., preferably between 165° C. and 215° C.

In particular, the bottom fraction is extracted from the first longitudinal chamber at a temperature set between 170° C. and 250° C., preferably between 180° C. and 210° C.

In particular, the overhead fraction is extracted from the first longitudinal chamber at a temperature set between 165° C. and 195° C., preferably between 170° C. and 190° C.

In particular, the concentration of Pseudocumene in the feed of the first longitudinal chamber is set between 18% and 35% by volume, preferably it is set between 20% and 30% by volume.

In particular, the operating temperature range of the second longitudinal chamber is set between 160° C. and 220° C., preferably between 160 and 200° C., and the working pressure of the second longitudinal chamber is preferably the atmospheric pressure.

In particular, the overhead fraction is extracted from the second longitudinal chamber at a temperature set between 160° C. and 200° C., preferably between 160 and 180° C.

In particular, the bottom fraction is extracted from the second longitudinal chamber at a temperature set between 175° C. and 220° C., preferably between 175° C. and 200° C.

According to another aspect of the invention, the method provides the steps of: compressing at least one portion of the first overhead vapour fraction and/or the second overhead vapour fraction, which are withdrawn from the first longitudinal chamber and/or from the second longitudinal chamber, respectively, a compressed overhead vapour being obtained from this compression at a pressure higher than the first/second working pressure, respectively, the compression step increasing the condensation temperature of the overhead vapour up to a value that is higher than the boiling temperature of a bottom fraction selected among the first bottom fraction and/or the second bottom fraction;

condensing the compressed overhead vapour, with a release of a condensation latent heat of the compressed overhead vapour;

heating and reboiling at least one part of the first bottom fraction and/or of the second bottom fraction, with an absorption of a required heat, wherein at least one part of the required heat is obtained from the condensation latent heat.

In particular, the step of compression is carried out at a compression ratio set between 1, 5:1 and 5:1, more in particular, at a compression ratio set between 1, 5:1 and 3:1.

In particular, the step of compression is carried out by compressing at least one portion of the first overhead vapour fraction, the compression increasing the condensation temperature of the overhead vapour up to a value that, advantageously, is higher than the boiling temperature of the second bottom fraction, and the step of heating and reboiling is carried out on at least one part of the bottom fraction that is extracted from the second chamber.

In particular, the heating step comprises a step of feeding the compressed vapour and the at least one part of the first/second bottom fraction to an indirect heat exchange apparatus, in particular, to a surface heat exchanger.

This way, the bottom reboiler operating costs are remarkably lower. The end-compression pressure is selected as a balanced value, in order to obtain a condensation temperature of the compressed gas that is high enough to allow the transfer of the required heat with an acceptable exchange surface of the indirect heat transfer apparatus, but that also limits the size of the compressors and their investment and operating costs. Furthermore, the large-sized and expensive prior-art-fashioned condensers of the two fractionation chambers, are sensibly reduced in size, or become unnecessary. Furthermore, the condensation of the overhead vapour in the reboiler of the column is a particularly advantageous solution, when required, for example in cased of poor availability of demineralised water for ordinary surface condensers, and/or in case of unavailability of steam at an enthalpy level suitable for use in reboilers and/or in case of difficulty to use a low-pressure steam which could be produced, alternatively, using the condensation heat of the overhead vapour from the distillation chambers.

In particular, if preferable, an amount of the compressed vapour may be used for generating steam.

The process may also comprise a step of direct condensation of at least one part of the overhead vapour that is extracted from the first longitudinal chamber and/or from the second longitudinal chamber, in particular, if reflux steps are provided like in the common distillation technique, i.e. if steps are provided of feeding to the first longitudinal chamber and/or to the second longitudinal chamber, an amount of condensed vapour that is extracted from the first longitudinal chamber and/or from the second longitudinal chamber.

Alternatively, or in addition, the condensation of the vapour extracted from the first longitudinal zone, and/or from the second longitudinal zone, may be carried out by well-known techniques and equipment, for example by air heat exchange, in an air-cooler, by air heat exchange, in a surface condenser or, preferably, in a steam generator by evaporating demineralized water.

Advantageously, the step of compression of the overhead vapour extracted from the first longitudinal chamber and/or from the second longitudinal chamber is carried out in a single step of compression.

Advantageously, the pressure of the compressed vapour, as obtained from the overhead vapour that is extracted from the first longitudinal chamber and/or from the second longitudinal chamber, is set between 1.5 and 5 bars; in other words, if the working pressure of the first longitudinal chamber or of the second longitudinal chamber is atmospheric, respectively, the compression of the compressed vapour is carried out at a compression ratio set between 1.5:1 and 5:1.

Preferably, this compression ratio is set between 1.5:1 and 3:1.

Advantageously, the proportion of the amount of the overhead vapour that is extracted from the first longitudinal chamber and/or from the second longitudinal chamber and is compressed, without any previous condensation, as well as the pressure of the compressed vapour, are selected in such a way that all the heat that is required for heating and boiling the at least one portion of the first/second bottom fraction is obtained from the condensation latent heat of the compressed gas. In other words, in this case the only heat source for the bottom product evaporation devices of at least one column is obtained by compressing a relevant portion of the overhead vapour produced by one of the two fractionation zones, apart from when starting up and/or shutting down the apparatus.

In another exemplary embodiment, the first overhead vapour fraction is completely supplied to the second longitudinal chamber, and the method also comprises a step of introducing into the first longitudinal chamber:
  a condensate from at least one part of the second overhead vapour fraction, and/or
  at least one part of the second bottom fraction, which forms the reflux for first chamber.

In particular, a step is provided of prearranging a catalytic fractionation means arranged in the first longitudinal chamber, said catalytic fractionation means arranged at a height above a feed port of the first longitudinal chamber, and a step of alkylating the aromatic hydrocarbons with olefins that are contained in the raw mixture, wherein the olefins are brought to a residual concentration lower than 4 ppm, preferably to a residual concentration lower than 1 ppm. This allows removing the olefins, in particular, the olefins with 9 or 10 carbon atoms, which distillate together with Pseudocumene, until a residual concentration is attained which cannot affect the purity degree of Pseudocumene to such an extent that would be unacceptable for further industrial conversion processes. The olefins may be present in the reforming-produced aromatics, if a removal step is poor or absent, at a feed concentration exceeding 100 ppm, but normally below 300 ppm.

The catalytic material may comprise acid earths, for example an acid earth as Engelhard F-54, which is now available from BASF, or an acid earth as Tonsil®, which is available from Sud-Chemie Furthermore, or alternatively, the catalytic material may comprise zeolites, in particular, a Zeolite Beta or MCM-22.

The catalytic material may also comprise a combination of the above materials and of any other catalytic material that is suitable for promoting alkylation.

In particular, said step of alkylation occurs by an alkylation reaction that is carried out at an alkylation temperature set between 160° C. and 190° C.

In particular, the catalytic fractionation means has the form of a packed bed of the first longitudinal chamber, and said step of alkylation occurs at a predetermined value of the spatial speed of the fractionating liquid phase that crosses this packed bed, i.e. at a predetermined value of the amount of liquid that crosses a volume unit of the packed bed. Such spatial speed is preferably set between $1.0\ h^{-1}$ and $10\ h^{-1}$, more in particular, is set between $2.0\ h^{-1}$ and $5.0\ h^{-1}$.

According to another aspect of the invention, the above mentioned objects are achieved by an apparatus for separating and recovering Pseudocumene from a raw mixture containing aromatic hydrocarbons with nine carbon atoms and preferably hydrocarbons with more than nine carbon atoms, the apparatus comprising:
  a first chamber and a second chamber, the first chamber adapted to receive the raw mixture;
  a first feed means for feeding the first chamber with the raw mixture;
  a first top extraction means for extracting a first overhead vapour fraction from the first chamber;
  a first bottom extraction means for extracting a first bottom fraction from the first chamber;
  a second feed means for feeding the second chamber with a stream selected between a portion of the first overhead vapour fraction and a portion of the first bottom fraction;
  a second top extraction means for extracting a second overhead vapour fraction from the second chamber;
  a second bottom extraction means for extracting a second bottom fraction from the second chamber;
  a maintenance means for maintaining the first chamber and the second chamber within predetermined working temperature ranges and at predetermined respective operating pressures;
wherein the maintenance means is adapted to maintain working temperature ranges and/or operating pressures such that:
  Pseudocumene is present substantially in only one fraction selected among the first overhead fraction and the first bottom fraction, and
  substantially pure Pseudocumene is contained only in one fraction selected among the second overhead fraction and the second bottom fraction, according to whether the Pseudocumene-containing fraction that is extracted from the first longitudinal chamber is the first bottom fraction or the first overhead fraction, respectively,
wherein the apparatus comprises an elongated container that is adapted to be arranged vertically, wherein an inner partition wall is arranged within the elongated container, the inner partition wall defining within the elongated container the first chamber and the second chamber,
wherein the main feature of the apparatus is that it comprises a differential expansion compensation means for compensating the differential expansion due to a temperature difference between said first chamber and said second chamber.

Preferably, the inner partition wall is substantially vertical.

The inner partition wall may have a shape selected from the group consisting of:
  a wall comprising at least one portion which extends according to a plane;
  a wall comprising at least one portion having a curvilinear cross section;
  a wall having a curvilinear and/or rectilinear closed cross section.

The position of the inner partition wall may be selected according to the composition of the raw mixture and/or according to the relative difficulty of the separations that are carried out in the first chamber and in the second chamber;

In particular, the inner partition wall is a substantially diametrical wall.

In an exemplary embodiment, the inner partition wall has an inner passageway, the passageway extending between a top section of the first chamber and a feed section of the second chamber, the passageway adapted to convey a stream of vapour between the first chamber and the second chamber and/or vice-versa.

This way, it is not necessary to prepare and to build a piping to connect the first chamber and the second chamber in order to extract the overhead Pseudocumene-containing fraction that is extracted from the first chamber and to feed it into the second chamber which allows a remarkable simplification and reduces construction time and costs, besides limiting the possibility of leakage of hydrocarbons/air from/to the process.

In an exemplary embodiment, a transverse inner partition wall is provided within the container, which defines along with the inner longitudinal partition wall the first longitudinal chamber and the second longitudinal chamber, such that a continuation portion of the first chamber is arranged on the same side of the second longitudinal chamber with respect to the inner longitudinal partition wall, and such that the inner longitudinal partition wall fluidically separates the continuation portion of the first chamber from a main portion of the first chamber, and furthermore
  said first bottom extraction means is arranged on the continuation portion of the first chamber;
  said main part of the first chamber comprises a bottom feed means;
  said container also comprises:
    a top feed means for feeding a liquid stream into an upper portion of the third chamber;
    a third top extraction means for extracting a third overhead vapour fraction (32,42,52) from the third chamber;
    a third bottom extraction means for extracting a third bottom fraction from the third chamber;

and wherein
a pneumatic connection is provided of the top feed means of the third continuation portion of the first chamber with the first extraction means of the first chamber, and said third top extraction means is pneumatically connected with the bottom feed means of the main part of the first chamber, in order to provide a continuous fractionation path of the stream of vapour between the main part and the continuation portion of the first chamber, at opposite sides of the inner longitudinal partition wall. This allows to limit the height of the column. In fact, the distillation of the raw mixture requires much more theoretical stages with respect to the subsequent separation, from which pure Pseudocumene is obtained as a bottom product or as a top product. By dividing the first chamber, in which the distillation of the raw mixture is carried out, into a main part and a continuation portion, the main part extending for the whole height of the column, and the continuation portion made at the opposite side of the longitudinal wall, it is no more necessary that the column has the same height as the height required for the distillation of the raw mixture.

Advantageously, the second chamber and the continuation portion together comprise a number of separation stages that is substantially the same as the number of stages of the main part of the first chamber. For instance, the second chamber and the continuation portion, on the one hand, and the main part, on the other hand, comprise the same number of trays or substantially the same packed bed height.

In an exemplary embodiment, the pneumatic connection comprises a further passageway that is defined within the inner longitudinal partition wall between the top feed means of the third continuation portion of the first chamber and the first extraction means of the first chamber. This way, it is not necessary to prepare and to build a piping to connect the first chamber and the second chamber to provide a connection between the main part and the continuation portion of the first chamber, which allows a further simplification and further reduces construction time and costs, besides further limiting the possibility of leakage of hydrocarbons/air from/to the process.

According to another aspect of the invention, the apparatus also comprises:
a compression means for compressing at least one portion of the first overhead vapour fraction and/or at least one portion of the second overhead vapour fraction, the compression means adapted to provide a compressed overhead vapour at a compressed vapour pressure such that the compressed overhead vapour has a condensation temperature that exceeds a boiling temperature of the first bottom fraction and/or it has a condensation temperature that exceeds a boiling temperature of the second bottom fraction;
a indirect heat exchange means between the compressed overhead vapour and at least one part of the first bottom fraction and/or at least one part of the second bottom fraction, the heat exchange means adapted to cause a boiling of at least one part of the first bottom fraction and/or a boiling of the second bottom fraction.

In particular, the indirect heat exchange means comprises a heat exchanger or a surface reboiler.

In particular, the compression means can be operated by an expansion means for expanding an aeriform substance and a heat exchange means, which is associated with at least one of the two chambers, is adapted to generate a stream of an aeriform substance, in particular, a saturated steam stream, said stream adapted to move the expansion means by operating the compression means, in particular, by a turbine, Advantageously, the compression means may be operated by an expansion means for expanding an aeriform substance, in particular by a turbine, and the apparatus comprises a generator of this aeriform substance.

Preferably, the generator of the aeriform substance comprises a saturated steam generator that is associated with a heating means of the first bottom fraction and/or of the second bottom fraction.

Advantageously, the saturated steam is generated by at least partially condensing the vapour that flows out of the outlet port of one chamber or of the other chamber within a water condenser/evaporator. The steam that is generated this way may be superheated in the convective part of an oven or of a bottom reboiler of one chamber.

Advantageously, the boiling zone that is associated with the first chamber and/or with the second chamber comprises a falling film reboiler. Such solution makes it possible to reduce the temperature difference between the beginning and end of the evaporation, and therefore the temperature difference between the boiling fluid and the condensing fluid, which allows saving the compression power that is required for the compressors that are associated with the first compression zone and/or with the second compression zone, with respect to the common vertical thermosiphon reboilers, with respect to the horizontal Kettle reboilers, and with respect to other conventional reboiler types. It also allows preventing possible cokization within the column bottom portion, which would unfavourably affect the colour of the product. The use of a falling film reboiler is particularly indicated if substantially pure Pseudocumene is extracted from the second longitudinal chamber as the overhead fraction, due to the higher condensation temperature the fraction heavy hydrocarbons-comprising fraction has with respect to pure Pseudocumene and due to the lower difference between the bottom fraction boiling temperature and the heating fluid supplied to the reboiler.

The possible ways to provide the compression apparatus that is required to set the invention into practice are well known to a skilled person.

Preferably, the compression of the overhead vapour that is extracted from the first chamber and/or from the second chamber is carried out in an electrically operated compressor, advantageously, in a centrifugal compressor or in a screw compressor. Such compressor provides construction and consumption materials, such as lubricants for seals and bearings, which are adapted to resist the relatively high temperature the overhead vapour has during the compression.

Advantageously, the extraction means for extracting the first bottom fraction from the second chamber comprises a side outlet port that is arranged at a predetermined height above the lower end of the second chamber, in order to extract the bottom fraction as a side cut. Preferably, the apparatus comprises a bottom discharge port of the second chamber, for removing a purge stream from the second chamber. Such solution is particularly advantageous if Pseudocumene is withdrawn from the second chamber substantially as a bottom fraction, since it allows withdrawing a particulate-free pure Pseudocumene, in particular without rust, which could settle in the bottom section of the second chamber, where a liquid head has to be present, i.e. an amount of liquid must be provided for operating the reevaporation means. In particular, in the case of a tray fractionation chamber, pure Pseudocumene may be withdrawn from at least one tray located above the lowest tray or stage of the second chamber.

In particular, the first chamber and/or the second chamber comprises distillation trays for performing respective distillation steps, wherein the distillation trays are preferably low pressure-drop trays.

Alternatively, the first chamber and/or the second chamber comprises at least one packed bed. Advantageously, the packed bed is a structured packed bed.

The first and/or the second chamber may also comprise a combination of distillation trays and of packed beds.

Preferably, a distillation tray, or a packing height corresponding to a distillation tray, is suited to cause a pressure drop, in the operating conditions of the column, lower than 20 millibar, preferably lower than 10 millibar, even more preferably lower than 2.5 millibar, which are values that can be obtained by particular structured packings, in order to limit the pressure drop through the first chamber and/or through the second chamber, and therefore in order to limit the compression power that is required by the compression apparatus that is associated with the first second distillation chamber and/or with the second distillation chamber. This way, it is possible to limit the pressure drop through the first chamber and/or through the second chamber, and therefore it is possible to limit the compression power that is required by the compression apparatus that is associated with the first second distillation chamber and/or with the second distillation chamber.

In a particular exemplary embodiment, the first chamber comprises a catalytic fractionation means that is arranged at a height above a feed port of the first longitudinal chamber, the catalytic fractionation means adapted to promote an alkylation reaction of the aromatic hydrocarbons with the olefins that are contained in the raw mixture, bringing the olefins from a feed concentration, which is normally set between 100 and 300 ppm, to a residual concentration that is lower than 4 ppm, preferably to a residual concentration that is lower than 1 ppm. In other words, the catalytic fractionation means is adapted to allow, together with the alkylation reaction, the mass exchange process to an extent that is required for the fractionation. This way, it is possible to remove such olefins, in particular, olefins with 9 or 10 carbon atoms, which distillate together with Pseudocumene, until a residual concentration is attained, which cannot reduce the purity degree of Pseudocumene to such an extent that would be unacceptable for most industrial conversion processes. In particular, the olefins may be present in the reforming-produced aromatics, if a removal step is poor or absent, at a feed concentration exceeding 100 ppm, but normally below 300 ppm.

In particular, the catalytic fractionation means comprises a catalytic material in the form of a packing material.

The catalytic material may comprise acid earths, for example an acid earth as Engelhard F-54, which is now available from BASF, or an acid earth type Tonsil®, which is available from Sud-Chemie The catalytic material may comprise, zeolites, in particular, a Zeolite Beta or MCM-22. This way, the catalytic material has a longer duration time, which may be about more than a year, and requires less frequent replacement stops The catalytic material may also comprise a combination of such materials, and of any other catalytic material that is suitable for promoting alkylation.

In particular, said maintenance means for maintaining the first chamber within predetermined temperature range are adapted to maintain the packed bed that comprises a catalytic material at an alkylation temperature set between 160° C. and 190° C.

In particular, said packed bed that comprises a catalytic material has a height such that the spatial speed of the liquid phase of the mixture that is being distilled is set between 1.0 $h^{-1}$ and 10 $h^{-1}$, more in particular, between 2.0 $h^{-1}$ and 5.0 $h^{-1}$.

In particular, a means is provided for setting said spatial speed, and said alkylation temperatures responsive to an expected useful life of the catalyst.

According to another aspect of the invention, a mass exchange column for exchanging mass between a first fluid stream that comprises a first fluid phase and a second fluid stream that comprises a second fluid phase, wherein the first fluid phase is selected between a liquid phase and a gas phase, wherein the second fluid phase is a liquid phase, the column comprising:

a vertical elongated container that is provided with a longitudinal dividing wall within the container, said container defining together with the dividing wall at least a first exchange chamber and a second exchange chamber;

a feed means for feeding the first chamber with the first fluid stream;

an extraction means for extracting the first fluid stream from the second chamber;

a source of the second stream;

an extraction means for extracting the second stream from said column, a contact means for causing a contact between the first stream and the second stream, the contact means arranged within the first exchange chamber and/or within the second exchange chamber;

a longitudinal passageway that extends between an outlet port of the first exchange chamber and an inlet port in the second exchange chamber, the passageway made in a proximity of the dividing wall, for conveying the first stream from the first exchange chamber into the second exchange chamber;

wherein the contact means and/or the passageway are such that in the passageway the first stream comprises an amount of a substance in the second fluid phase, whose main characteristic is that it comprises:

along the passageway, a phase-separation means that is adapted to receive the first stream and to form a main portion of the first stream and a secondary portion of the first stream, the secondary portion comprising at least a part of the amount of substance in the second fluid phase;

a feed means for feeding the main portion of the stream at a predetermined feed height of the second exchange chamber.

The above-defined phase-separation means allows removing the amount of substance in the second fluid phase from the first stream upstream of or at most at the inlet port of the second chamber.

In particular, the phase-separation means is provided comprising a feed means for feeding the secondary portion of the stream at a further predetermined feed height of the second exchange chamber.

In an exemplary embodiment, the phase-separation means comprises a decantation chamber made within the passageway.

Preferably, the decantation chamber has a height greater than or equal to twice the height of a theoretical stage of the second exchange chamber.

In particular, the decantation chamber has a height greater than or equal to 1000 mm, more in particular, a height greater than or equal to 1200 mm.

Preferably, the decantation chamber has a height greater than or equal to about ⅓ of an equivalent inner diameter of the column.

Preferably, the decantation chamber is adapted to separate the main portion of the first stream substantially in the gas/liquid phase, and has a second transverse dimension, which is defined perpendicularly to the first transverse dimension, greater than or equal to twice an equivalent diameter of an outlet port of the main portion of the first stream.

In an advantageous exemplary embodiment, the decantation chamber has a connection means for a level sensor for measuring the level of a head of the fluid phase of the highest specific weight in the decantation chamber. The level sensor may be associated with a flow rate-control logical unit for the highest specific weight portion that is supplied into a lower section, or in any case into any zone of the exchange chamber that is suitable for carrying out the subsequent steps, the logical unit operatively connected with a flow rate regulation means, in particular, by a regulation valve, in order to operate the regulation means responsive to the level of the head.

BRIEF DESCRIPTION OF THE DRAWINGS

The invention will be now shown with the description of an exemplary embodiment thereof, exemplifying but not limitative, with reference to the attached drawings, wherein:

FIGS. 12A and 12B show a cross sectional view of different exemplary embodiments of the passageway defined by the inner longitudinal partition wall;

FIG. 13 shows an alternative exemplary embodiment of a distillation column equipped with inner partition wall, in which column sections of different diameter are provided;

FIG. 16 is a diagrammatical longitudinal sectional view of a mass transfer column according to an exemplary embodiment of the invention, wherein a passageway is provided between a first exchange chamber and a second exchange chamber that are arranged within the partition wall;

FIG. 17 is a diagrammatical longitudinal sectional view of a mass transfer column according to another exemplary embodiment of the invention, wherein two passageways are provided between a first exchange chamber and a second/third exchange chamber, in which the passageways are arranged within the dividing wall;

FIG. 18 is a diagrammatical cross sectional view of a mass transfer column according to the previous exemplary embodiments of the invention;

FIG. 19 is a diagrammatical longitudinal sectional view of a mass transfer column according to a further exemplary embodiment of the invention, wherein a passageway is provided between a first exchange chamber and a second exchange chamber that are arranged immediately proximate to the dividing wall;

FIG. 20 is a diagrammatical cross sectional view of the mass transfer column of FIG. 19;

FIG. 21 is a diagrammatical longitudinal sectional view of a mass transfer column according to an exemplary embodiment of the invention, in which the phase-separation means is provided with distribution and feed means of heterogeneous phases into respective portions of a second exchange chamber;

FIG. 22 is a diagrammatical longitudinal sectional view of the phase-separation means according to an exemplary embodiment;

FIG. 23 is a cross sectional view of the phase-separation means of FIG. 7;

FIG. 24 is a further a longitudinal sectional view of the phase-separation means according to FIG. 7;

In the figures, similar components or components that have similar functions, have been indicated by the same numbers. In particular, for the sake of conciseness, the reference numbers written close to process and utility lines may relate both to the lines and to the streams that flow within these lines.

DESCRIPTION OF PREFERRED EXEMPLARY EMBODIMENTS

Figure 2A:
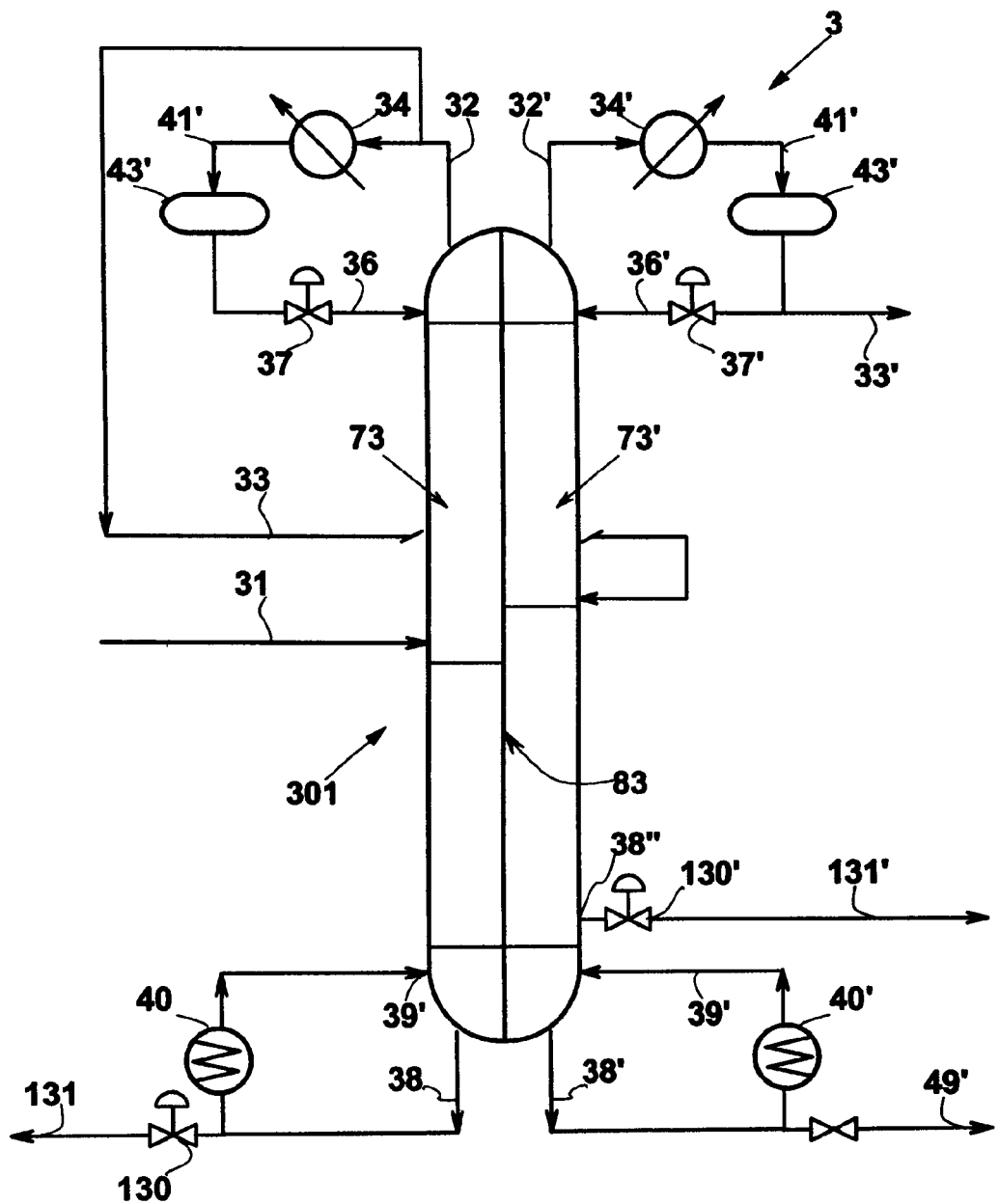
FIGS. 2A and 2B show a process flow diagram, according to the invention, for separating Pseudocumene from a C9 or C9+ aromatic hydrocarbon mixture, by two fractional distillation operations that are carried out within inner longitudinal chambers of a single distillation column, the one separated from the other.

In FIG. 2A an apparatus 3 is diagrammatically shown, according to an alternative exemplary embodiment of the invention, for separating and recovering Pseudocumene from a raw mixture 31 that comprises, besides Pseudocumene, other aromatic hydrocarbons with 9 or more than nine carbon atoms, and possibly minor amounts of hydrocarbons with less than nine carbon atoms. The apparatus comprises a distillation column consisting of an elongated, vertically arranged cylindrical container 301 that has an inner partition wall 83. Inner partition wall 83 defines two longitudinal distillation chambers 73 and 73' within container 301, that are associated to a means 40,40' for maintaining predetermined respective working temperature profile or distribution in the presence of a process fluid, and to a means for maintaining a predetermined working pressure, which are arranged at a position not shown of the line by which a light fraction 33' is withdrawn, in particular, for maintaining a substantially atmospheric working pressure.

Apparatus 3 is suitable for carrying out the method according to the invention. In fact, raw mixture 31 is supplied, in particular, to first chamber 73 through an inlet port made at an intermediate section, and is caused to pass through first chamber 73, where distillation conditions are maintained. A stream of a overhead vapour fraction 32, which contains lighter aromatic hydrocarbons, is extracted from distillation chamber 73; an amount 41 of this fraction is condensed in a heat exchanger or condenser 34 and temporarily stored within a storage tank 43, to be then reintroduced into distillation chamber 73 through an inlet port made at an upper portion of chamber 73, wherein a reflux stream 36 is formed according to a predetermined reflux ratio. The flow rate of reflux stream 36 is controlled by well-known methods and means, typically by a regulation device comprising a regulation valve 37 whose opening is controlled by the level of storage tank 43.

A stream 38 of a bottom fraction is extracted as a liquid from a bottom section of first chamber 73, an amount 39 of which is supplied to a reboiler 40 where it is caused to boil and preferably heated, receiving enough heat to separate by distillation lighter and heavier products that are contained in the raw mixture, which takes place in first chamber 73. Stream 39 of the vaporized bottom fraction is recycled into first distillation chamber 73, where it releases the fractionation heat and allows a predetermined temperature profile to be established, responsive to the chemical-physical properties of the hydrocarbon mixture that is treated in first distillation chamber 73.

The operating parameters of the column, in particular the reflux ratio and the amount of heat, may be predetermined in such a way that different temperature profiles may be obtained along the first distillation chamber, and therefore different concentration profiles of each component that is present in the raw mixture, along the first distillation chamber. This way, if a sufficient number of stages is available, it is possible to operate such that Pseudocumene is present as the main component in the overhead fraction or in the bottom fraction, in particular, such that it is present substantially only in stream 32 of the overhead vapour fraction or substantially only in stream 38 of the fraction, whereby a Pseudocumene-containing fraction and a substantially Pseudocumene-free mixture are extracted from the first longitudinal chamber.

FIG. 2A relates to the case in which Pseudocumene is present as the main component, or substantially alone in stream 32 of the overhead vapour fraction. Therefore, a stream 33 of overhead vapour is supplied as such to second chamber 73' for separating Pseudocumene from aromatic hydrocarbons that are lighter than Pseudocumene. Even if in FIG. 2A, and in other subsequent drawings, only the case is shown of a vapour phase hydrocarbon mixture feed, it is possible to feed the second distillation chamber with a liquid or with a liquid-vapours mixture, which contains such lighter products.

A amount 131 of stream 38 of the bottom fraction that is extracted from the first distillation chamber 301, and contains C9 or C9+ hydrocarbons heavier than Pseudocumene, is withdrawn as the bottom product of fractionation unit 3. The flow rate of withdrawn stream 131 is controlled by well-known methods and means, typically by a regulation device comprising a regulation valve 130 whose opening is controlled by the liquid level of a bottom section of chamber 73 or, in other exemplary embodiments, of the main body of reboiler 40.

Stream 33 of overhead vapour is supplied to second chamber 73' through an inlet port made at an intermediate section, and is caused to pass through second chamber 73', where distillation conditions are maintained. A stream of a overhead vapour fraction 32', which contains aromatic hydrocarbons lighter than Pseudocumene, is extracted from distillation chamber 73'; an amount 41' of this fraction is condensed in a heat exchanger or condenser 34' and temporarily stored within a storage tank 43', to be then reintroduced into distillation chamber 73' through an inlet port made at an upper portion of chamber 73', wherein a reflux stream 36 is formed' according to a predetermined reflux ratio. Even in this case, the flow rate of reflux stream 36' may be controlled in a well-known way, typically through a regulation valve 37'

A stream 38' of a bottom fraction is extracted as a liquid from a bottom section of second chamber 73', an amount 39' of which is supplied to a reboiler 40' where it is caused to boil and preferably heated, receiving enough heat to separate by distillation lighter and heavier products that are contained in stream 33, which takes place in second chamber 73'. Stream 39' of the vaporized bottom fraction is recycled into second distillation chamber 73', where it releases the fractionation heat and allows a predetermined temperature profile to be established, responsive to the chemical-physical properties of the hydrocarbon mixture treated in second distillation chamber 73'.

The operating parameters of the column, in particular, the reflux ratio and the amount of heat, may be predetermined in such a way that different temperature profiles may be obtained along the first distillation chamber, and therefore different concentration profiles of each component that is present in stream 33, in particular, with a sufficient number of stages, it is possible to obtain substantially pure Pseudocumene in stream 38' of bottom fraction, and to withdraw a stream 33' of substantially pure Pseudocumene. Even in this case, the flow rate of withdrawn Pseudocumene 131' may be controlled conventionally, typically by a regulation valve 130 that is controlled by the liquid level of a bottom section of chamber 73'.

Figure 5:
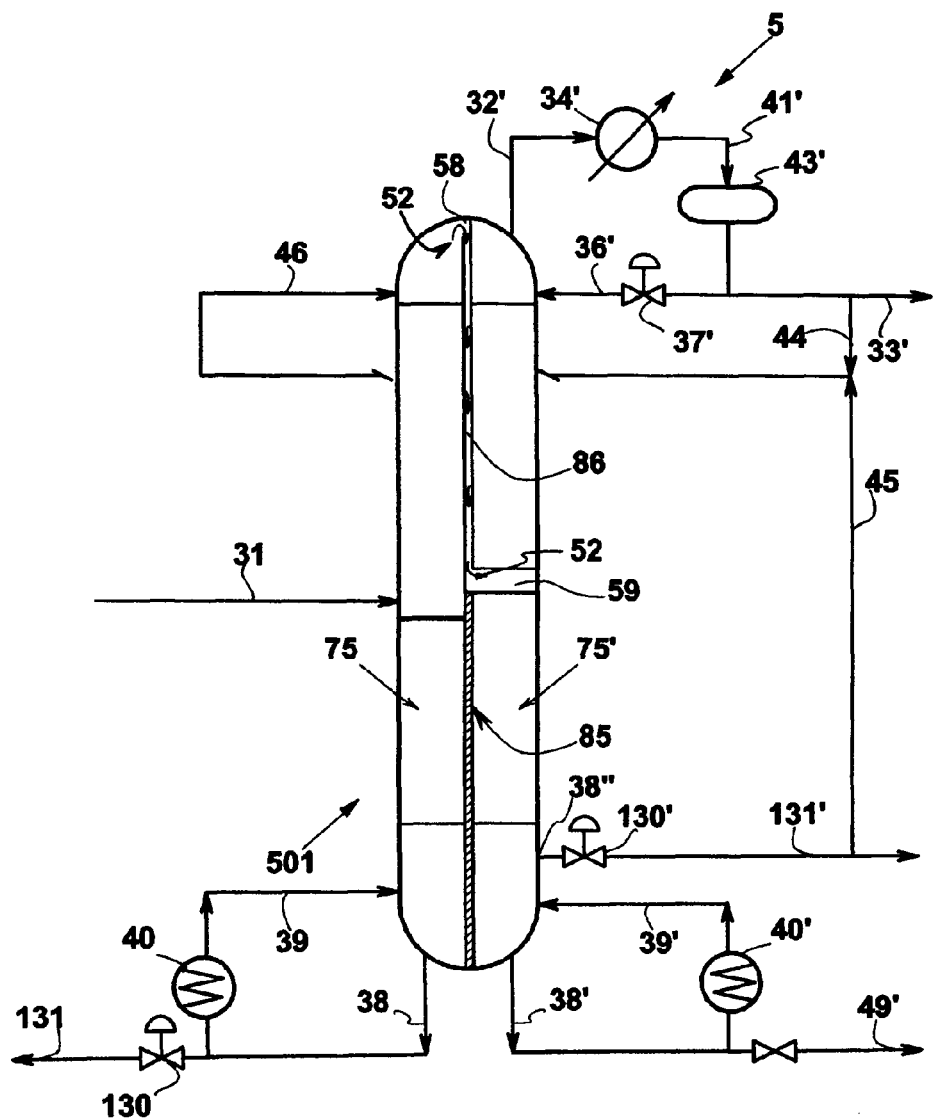
FIG. 5 shows process flow diagram equivalent to the one of FIG. 4, in which the inner partition wall defines an internal passageway for conveying the vapour that is extracted from the first chamber into the second distillation chamber.

FIG. 5 relates to the case in which Pseudocumene is present as the main component, or substantially alone, in stream 38 of the bottom fraction. Therefore, a stream 47 of the bottom fraction is supplied to second chamber 73' for separating Pseudocumene from heavier aromatic hydrocarbons.

An amount 33 of stream 32 of overhead vapour 41 that is extracted from first distillation chamber 301 and condensed, is withdrawn as light product from fractionation unit 3', and contains aromatic hydrocarbons lighter than Pseudocumene.

Stream 47 of bottom fraction is supplied to second chamber 73' through an inlet port made at an intermediate section, and is caused to pass through second chamber 73', where distillation conditions are maintained. A stream of a overhead vapour fraction 32' is extracted from second distillation chamber 73'; an amount 41' of this fraction is condensed in a heat exchanger 34' and temporarily stored within a storage tank 43', to be then reintroduced into distillation chamber 73' through an inlet port made at an upper portion of chamber 73', wherein a reflux stream 36' is formed according to a predetermined reflux ratio. Even in this case, the flow rate of reflux stream 36' may be controlled in a known way, typically through a regulation valve 37'.

A stream 38' of a bottom fraction is extracted as a liquid from a bottom section of second chamber 73', an amount 39' of which is supplied to a reboiler 40' where it is caused to boil and preferably heated, receiving enough heat to separate by distillation lighter and heavier products that are contained in stream 47, which takes place in second chamber 73'. Stream 39' of the vaporized bottom fraction is recycled into second distillation chamber 73', where it releases the fractionation heat and allows a predetermined temperature profile to be established, responsive to the chemical-physical properties of the hydrocarbon mixture treated in second distillation chamber 73'.

The operating parameters of the column, in particular, the reflux ratio and the amount of heat, may be predetermined in such a way that different temperature profiles may be obtained along the second distillation chamber, and therefore different concentration profiles of each component that is present in stream 33, in particular, with a sufficient number of stages, it is possible to obtain substantially pure Pseudocumene in stream 32' of overhead vapour, and to withdraw a stream 33' of substantially pure Pseudocumene, whereas an amount 131', which contains C9 or C9+ hydrocarbons heavier than Pseudocumene, is withdrawn as the bottom product from fractionation unit 3'. Even in these case, the flow rate of withdrawn aromatic heavy hydrocarbons 131' may be controlled conventionally, typically by a regulation valve 130 controlled by the liquid level of a bottom section of chamber 73'.

In FIGS. 3A to 3E a differential expansion compensation means is shown for compensating the differential expansion caused by the temperature difference between a first chamber 273 and a second chamber 273', of a distillation column 200 where a distillation is carried out of a mixture of hydrocarbons with 9 and more than 9 carbon atoms, to obtain pseudocumene. Chambers 273,273' are separated by a dividing wall 285.

Figure 3A:
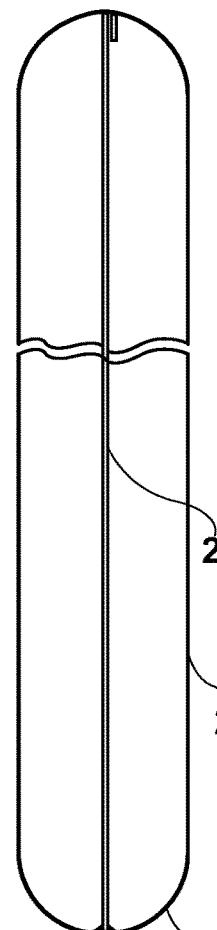
FIGS. 3A-3E show some exemplary embodiments of the means for compensating the differential expansion between the two distillation chambers.

According to a first in the exemplary embodiment of FIG. 3A, dividing wall 285 is internally connected to a shell of column 200 at an own short edge portion extension, whereas the other edge portions have a relative freedom of movement, which allows the expansion o dividing wall 285. For example, this edge portion may be welded to the shell, or it may be connected by any suitable connection technique.

Figure 3B:
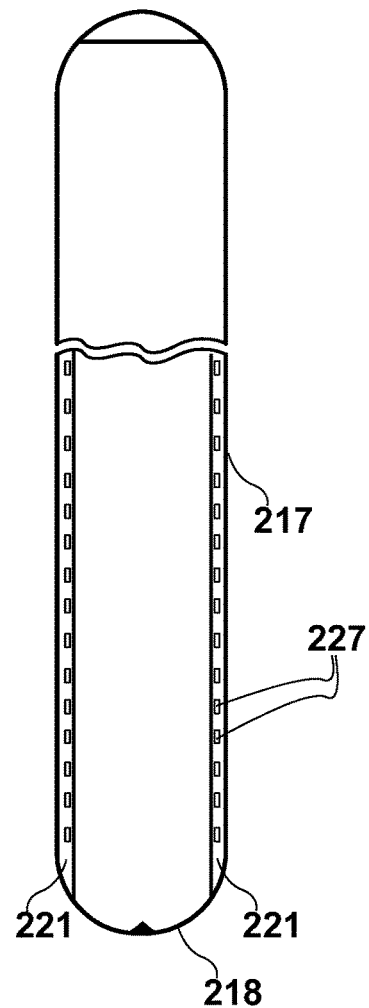
Figure 3C:
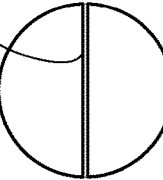
Figure 3D:
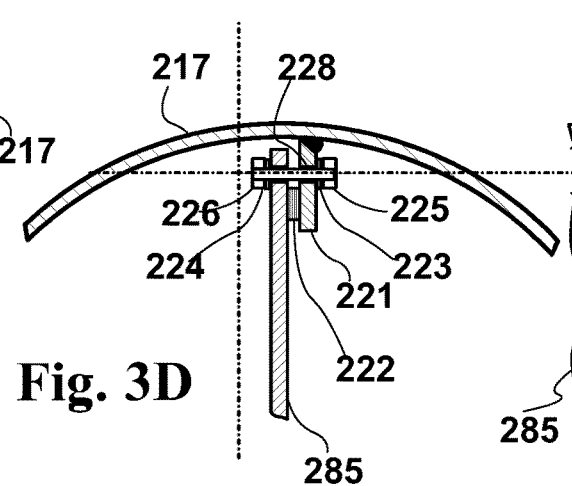
Figure 3E:
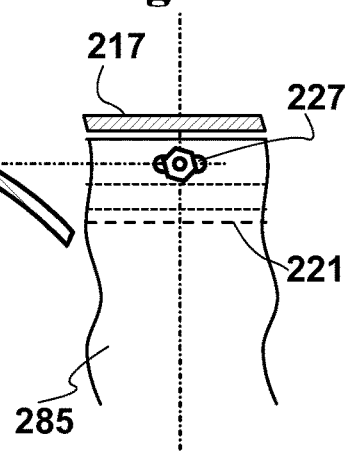

In the in the exemplary embodiment of FIG. 3B, the dividing wall is internally connected to a rounded bottom 218,219 of the column at an own end edge portion, preferably it is welded within lower end portion 218. In this case, a guide means is provided for guiding the longitudinal slide movement of dividing wall 285, the guide means preferably comprising a couple of longitudinal plates 221 that extend along the whole height of column 200. Also longitudinal plates 221 may be internally connected with the column, typically within the shell 217, by welding or by any suitable technique. Along the long sides of the longitudinal dividing wall, aligned holes 227 are made parallel to the edges. Similarly, near the edge of each longitudinal plate 21 aligned holes 228 are made parallel to the edge. Holes 227 and holes 228 have reciprocal distances according to a same pattern, so that each hole faces a hole during the slide movement of dividing wall 285 with respect to trays 221. In each couple of reciprocally facing holes 227 and 228 one hole is slotted and the other is circular, or in any case it is adapted to receive a tie-member 226, in particular, as shown in the picture, to receive stem portion of a screw. A nut 225 is arranged opposite to the screw head 226, and engages with the screw according to a prefixed blocking force. A seal 222 is arranged between longitudinal plate 221 and dividing wall 285, for example a Teflon® seal, which ensures the a fluid-tight contact between chamber 273 and chamber 273'. Materials are known that are well-suited to provide an acceptable seal at a pressure difference up to 1 bar, between the first chamber and the second chamber. A suitable seal means may be also be arranged at nut 225, as shown in the picture, or at screw head 226 that is located on the maximum pressure side.

The elongated holes may have an increasing length, moving away from the edge portion connected to the equipment, in this case away from the bottom of the apparatus, since the average thermal expansion is proportional to the distance from the constrained end. The locking the screws in the nuts, or of other equivalent screw threaded means, must ensure the seal between the chambers the seal provided by the gaskets 222 without hindering the slide movement of dividing wall 222.

Owing to this arrangement, dividing wall 285 can buckle under the action of thermal stress.

In another exemplary embodiment shown in the same picture, expansion compensation are provided means that are integrated in the dividing wall, and comprise a deformable portion of the dividing wall, to allow an expansion or in any case a thermally induced deformation.

A distillation column 200 is shown which comprises a container 211 having an inner dividing wall or baffle 85, which defines in the column two distinct distillation chambers 273 and 263'. An expansion compensation means is provided for compensating the differential expansion that is caused by the temperature difference between first chamber 73 and second chamber 73'.

In a first exemplary embodiment, the compensation means comprises a longitudinal slide guide 221 in the form of longitudinal plates, which are internally welded to the wall of the equipment. The compensation means comprises an inner dividing wall or baffle 285, in this case a diametrical wall, which is connected to a point of the equipment, for example at a lower top of it.

Figure 4:
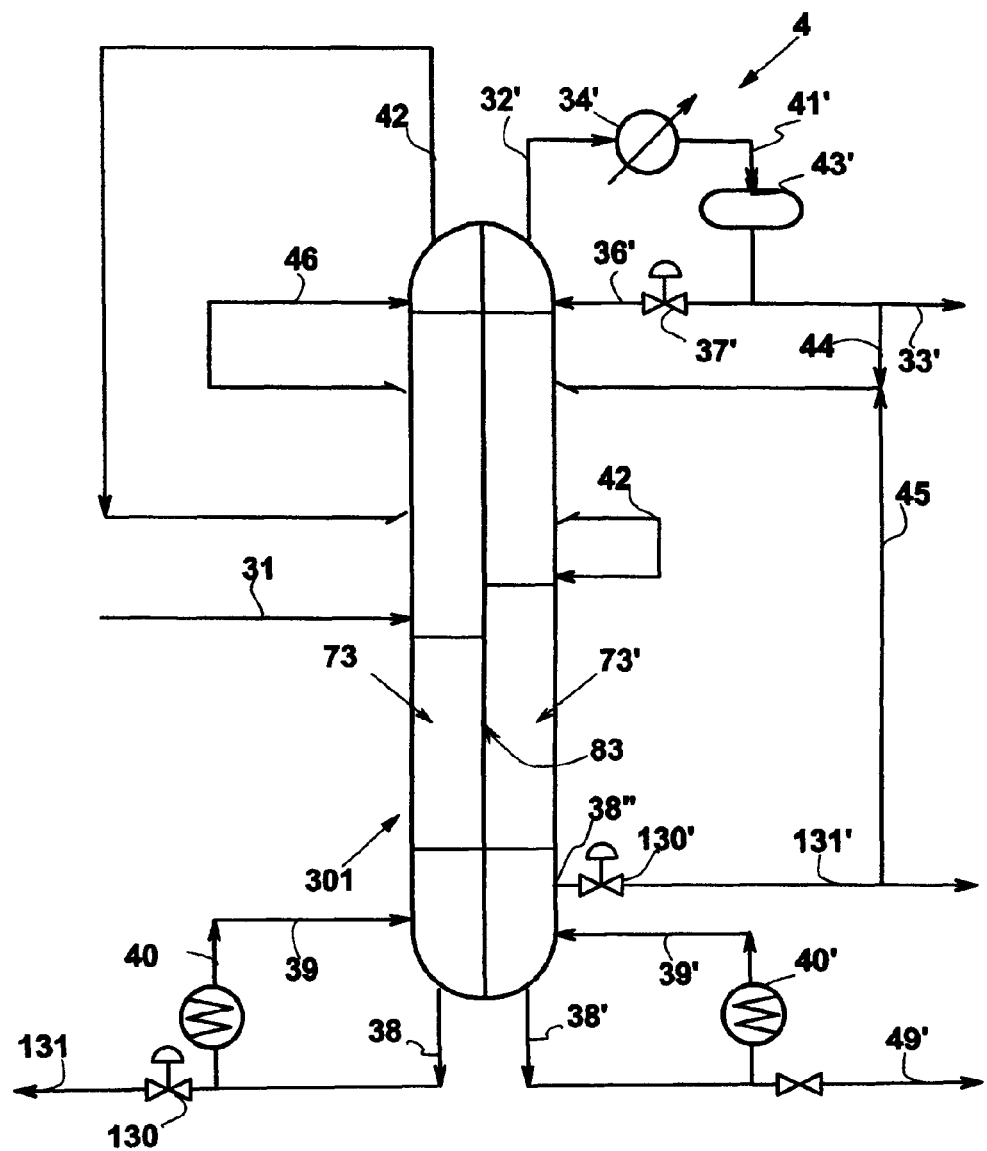
FIG. 4 shows a process flow diagram, in which the reflux stream of the first chamber is formed otherwise than in the diagram of FIG. 3A.

In FIG. 4 an apparatus 4 is diagrammatically shown, according to an alternative exemplary embodiment of the invention, which differs from apparatus 3 of FIG. 3A in that a stream 42 including all the overhead vapour extracted from first distillation chamber 73 is fed to second distillation chamber 73' of column 301. The reflux stream 46 of first distillation chamber 73 is then obtained by combining a stream 44, containing a part of the light aromatic hydrocarbons of the overhead fraction 32' of second chamber 73', with a stream 45 of substantially pure Pseudocumene of bottom fraction 38' of the same chamber 73'.

In FIG. 5 an apparatus 5 is diagrammatically shown, according to an alternative exemplary embodiment of the invention, which comprises a vertically arranged distillation column 501 consisting of an elongated container with an inner partition wall 85. Inner partition wall 85 defines two longitudinal distillation chambers 75 and 75' within container 301, which are similar to chambers 73 and 73' of distillation column 301; furthermore, inner partition wall 85 has an inner passageway 86 between an outlet port 58 made at the top section of first chamber 75, and an inlet port 59 of second chamber 75' of container 501. This passageway is adapted to convey a overhead vapour stream 52 from the top section of first longitudinal chamber 75 to inlet port 59 of second chamber 75', thus allowing second chamber 75' to be fed with a stream comprising all the overhead vapour that is extracted from first chamber 75, like in apparatus 4 of FIG. 4. Reflux stream 46 of first distillation chamber 75 is obtained as in the case of apparatus 4.

Figure 6:
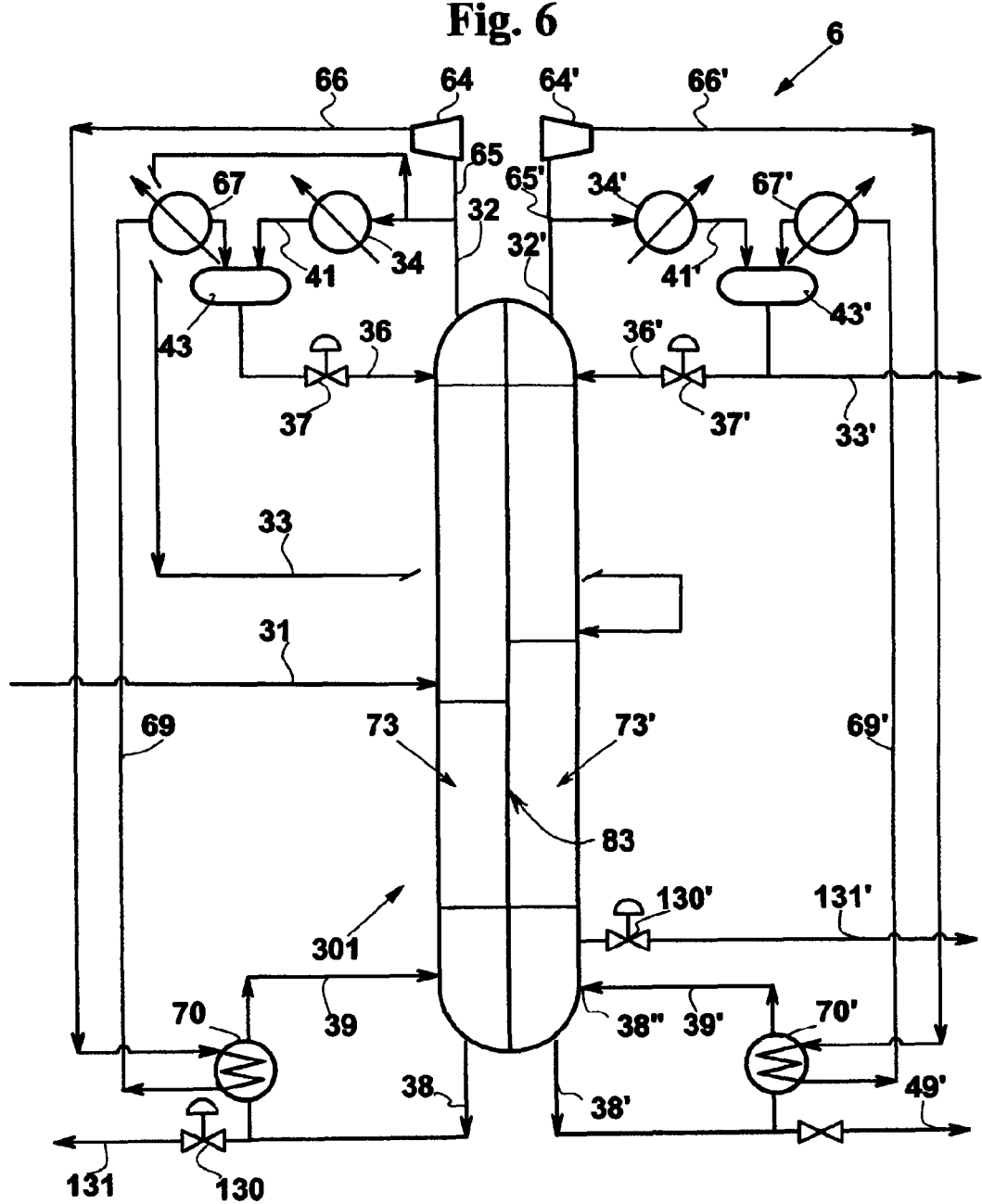
FIGS. 6 and 7 show process flow diagrams in which an amount of the overhead vapour that is extracted from each column is subject to direct compression to allow heat exchange for boiling respective streams of bottom fractions.

In FIG. 6 an apparatus 6 is diagrammatically shown, according to an alternative exemplary embodiment of the invention, which differs from apparatus 3 of FIG. 3A in that it comprises two compressors 64,64', in particular, one-stage compressors which are adapted to operate at a compression ratio set between 3:1 and 5:1, and are used for compressing streams of overhead vapour 65,65' obtained from streams 32 and 32', respectively. Compressed vapour streams 66,66' are used in exchangers 70,70' in which, by an at least partial condensation, release their condensation heat to streams 39 and 39' of bottom product, respectively. In the represented exemplary embodiment, the streams 69,69' of the vapour that are at least partially condensed in reboiler 70,70' are caused to pass through further condensers 67,67', respectively, where the condensation is completed, and then are collected into storage tanks 43, respectively.

Figure 7:
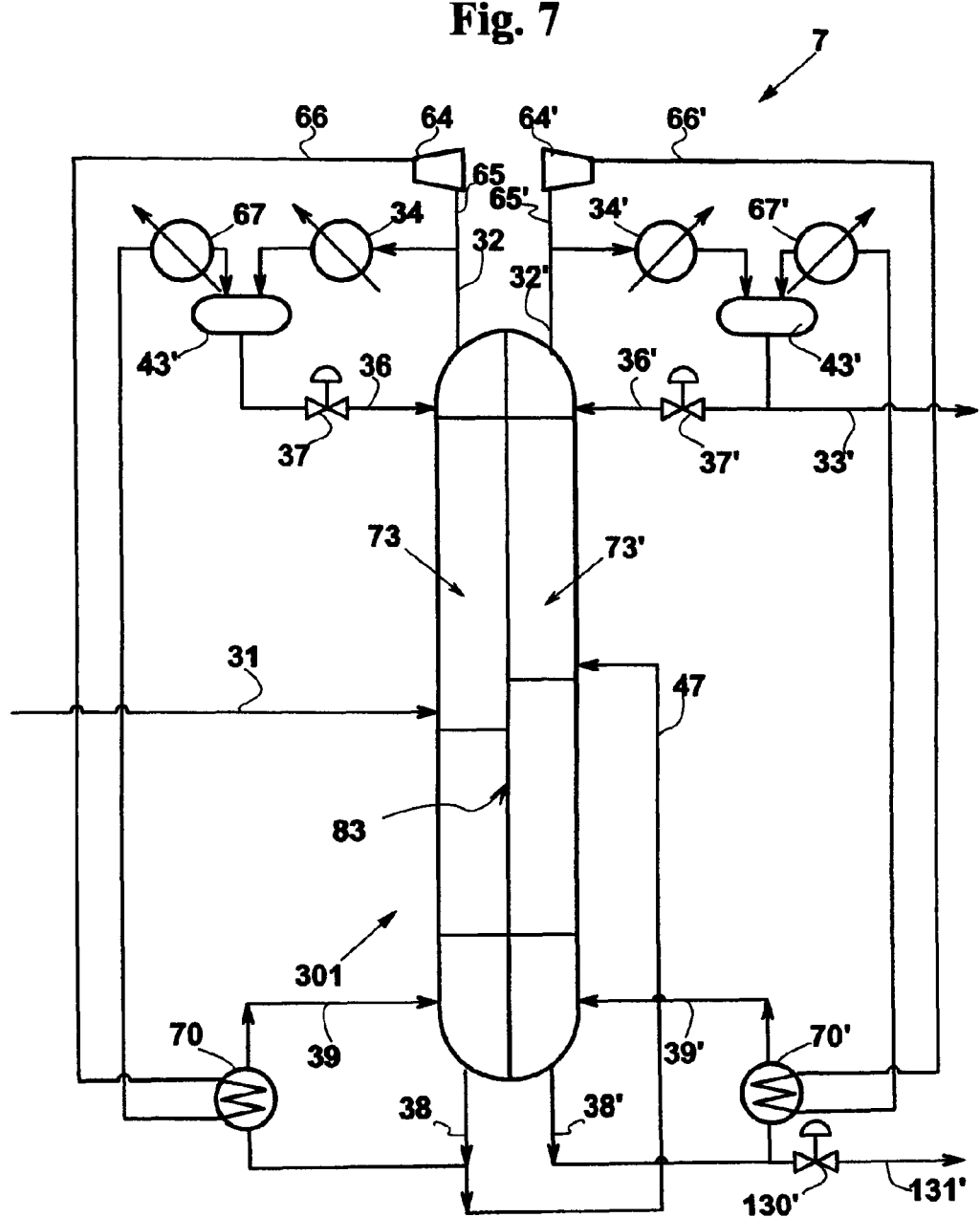

In FIG. 7 an apparatus 7 is diagrammatically shown, according to an exemplary embodiment of the invention, which differs from apparatus 6 of FIG. 6 in that the operating conditions of first chamber 73, in particular, the working temperature profile and the reflux ratio are selected such that, with the composition of raw mixture 31, Pseudocumene is present as the main component, or substantially pure, in stream 32 of the bottom fraction, if a sufficient number of stages is available. Therefore, an amount 47 of stream 38 of the bottom fraction that is extracted from first chamber 73' is supplied as such to second chamber 73' for separating Pseudocumene from aromatic hydrocarbons that are heavier than Pseudocumene.

Figure 8:
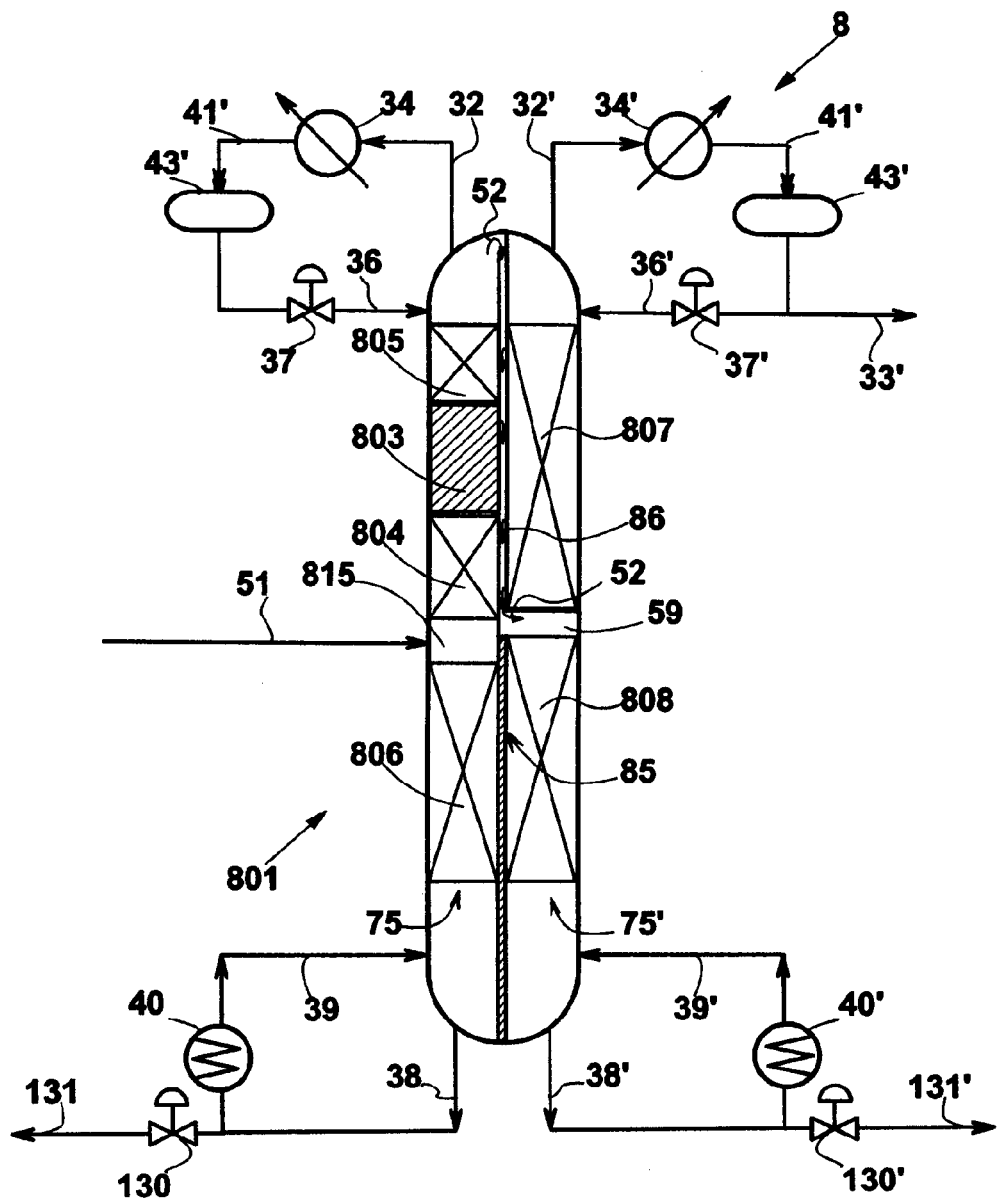
FIG. 8 shows a process flow diagram in which a catalytic bed is provided within the first chamber for converting of minor components of the raw mixture, in particular olefin components.

In FIG. 8 an apparatus 8 is diagrammatically shown, according to an exemplary embodiment of the invention, which is adapted to treat a raw mixture 51 containing determined concentration of olefins, in particular, olefins with 9 and/or 10 carbon atoms, at a concentration even higher than 100 ppm. To this purpose, at least one packing 803, preferably a structured packing, is arranged within first chamber 75, above a feed section 815 of raw mixture 51, which comprises a catalytic material that is adapted to promote, if a predetermined field of temperature is maintained, an alkylation reaction between the olefins and the C9 or C9+ aromatic hydrocarbons of the mixture, in order to reduce the content of olefins and to increase the content of useful alkylated aromatic hydrocarbons that can be separated from Pseudocumene by apparatus 8. Catalytic material containing packing 803 is also adapted to allow the mass exchange required by the fractionation, i.e. it is adapted to provide a useful packing height that corresponds to a predetermined number of stages, and in other words it is adapted to perform a reactive distillation step. The catalytic material may comprise acid earths, for example Engelhard F-54 acid earths, and/or Tonsil acid earths. The packing may be of a known type, for example a Katapac® commercially available from Sulzer or a Katamax packing commercially available from Koch-Glitsch. Depending upon the height of catalytic packing 803, column 801 may be adapted to give Pseudocumene, which in this case is withdrawn as bottom fraction 38',131' of second chamber 75', with a residual olefin concentration lower than 10 ppm, preferably a concentration lower than 4 ppm, much more preferably a concentration lower than 1 ppm.

First chamber 501 of column 801 comprises other packings 804,805 and 806, which also preferably consist of structured packed beds, in order to limit the pressure drop. Also the second distillation chamber 802 is a packed column, and comprises packings 807,808 in the upper section and in the lower section, respectively, i.e. above and below feed section 59. Even if the distillation means of column 801, as shown in FIG. 8, consist of packings or of structured packed beds, the case of at least one portion of first chamber and of second chamber 75,75' containing distillation trays falls within the scope of the invention.

As in the case of column 501 of apparatus 5 (FIG. 5), inner partition wall 85 has an inner passageway 86 for a stream of overhead vapour that is extracted from first chamber 75 and is fed into second chamber 75'. However, unlike apparatus 5, reflux stream 36 of first distillation chamber 75 is obtained by withdrawing a stream 32 of overhead vapour 32 from first distillation chamber 75 and condensing it in condenser 34, and is not obtained by combining streams that are extracted from second chamber 75'.

Figure 9:
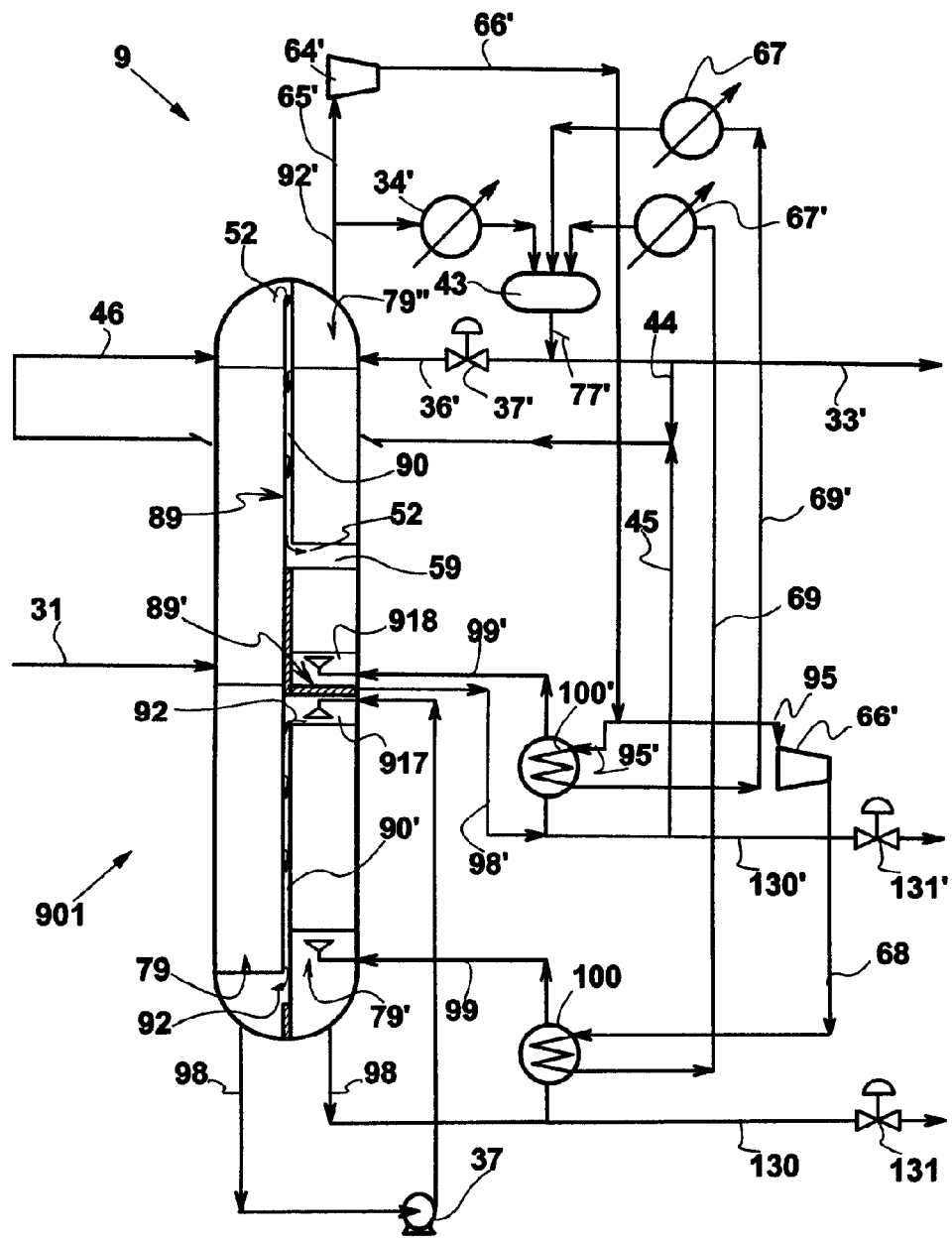
FIG. 9 shows a process flow diagram derived from the diagram of FIG. 5, in which a distillation chamber comprises two distinct chambers at opposite sides of the inner longitudinal partition wall.

In FIG. 9 an apparatus 9 is diagrammatically shown, according to an exemplary embodiment of the invention, comprising a distillation column 901. A transverse inner partition wall 89 is provided within said container, which defines along with said inner longitudinal partition wall 89' said first longitudinal chamber and said second longitudinal chamber 79", such that a continuation portion 79' of said first longitudinal chamber is arranged on the same side of said second longitudinal chamber 79" with respect to said inner longitudinal partition wall 89, and such that said inner longitudinal partition wall 89 fluidically separate said continuation portion 79" of said first chamber from a main portion 79 of said first chamber;

said first bottom extraction means is arranged on said continuation portion 79" of said first chamber;

said main part 79 of said first chamber comprises a bottom feed means;

said container also comprises:
  a top feed means for feeding a liquid stream into an upper portion of said third chamber;
  a third top extraction means for extracting a third overhead vapour fraction 32,42,52 from said third chamber;
  a third bottom extraction means for extracting a third bottom fraction 38,98 from said third chamber;
  and wherein
a pneumatic connection 90' is provided of said top feed means of said continuation portion 79" of said first chamber with said first extraction means said first chamber, and
said third top extraction means is pneumatically connected with said bottom feed means of said main part 79 of said first chamber, such that a continuous fractionation path of said stream of vapour 92 is provided between said main part 79 and said continuation portion 79" of said first chamber 79', at opposite sides of said inner longitudinal partition wall 89.

With reference to FIG. 5, a distillation column 901 comprises an inner longitudinal partition wall 89 that defines a first passageway 90 for a stream of overhead vapour 52 extracted from main part 79 of the first chamber and fed into continuation portion 79''' of the first chamber. Still like apparatus 5, reflux stream 46 supplied to first space 79 is obtained by joining a stream 44 with a stream 45. Stream 44 comprises a part of the light aromatic hydrocarbons extracted as overhead fraction 92' from distillation portion 79''', whereas stream 45 comprises substantially pure Pseudocumene extracted as bottom fraction 98'. Bottom fraction 98' is withdrawn from the same space 79''', upstream of the branch by which the stream of substantially pure Pseudocumene 130' is withdrawn. A second, substantially horizontal inner partition wall 89' defines along with first inner partition wall 89 and along with container 11 of column 901 a second space 79' and a third space 79''. Second space 79' is located below second inner partition wall 89', whereas third space 79'' is located above second inner partition wall 89'. A pump 37 is provided for extracting a bottom stream 98 from space 79 and for sending this stream to a top section 917 of second space 79'. Furthermore, inner partition wall 89 defines a second passageway 90' between a top section 917 of second space 79' and a bottom section of the first space, which is adapted to convey a stream 92 of overhead vapour between top section 917 of space 79' and the bottom of space 79. This way, first space and second space 79,79' form a single distillation chamber comprising two spaces 79,79', which are arranged at opposite sides of column 901, as defined by first inner longitudinal partition wall 89.

Independently from the above-described space distribution, apparatus 9 comprises compressors 64,64', which are adapted to work with respective compression ratios set between 1.5:1 and 5:1. Second compressor 64' is used for compressing a stream 65' of overhead vapour 92' that is withdrawn from second distillation chamber 79'''. A first amount 95' of so obtained compressed vapour stream 66' is used in exchanger 100' in which, by an at least partial condensation, it releases its own condensation heat to stream 98' of the bottom product that is extracted from the second distillation chamber, i.e. from third space 79'' of column 901. First compressor 64 is used for compressing a second amount 95' of vapour 66' already compressed by second compressor 64', thus obtaining a further compressed vapour 68 that, by an at least partial condensation in exchanger 100, releases its own condensation heat to stream 98 of the bottom product extracted from the first distillation chamber, which comprises first space 79 and second space 79'. Streams 69,69' of vapour at least partially condensed in reboiler 100,100' are introduced into further condensers and/or refrigerants 67,67', respectively, where the condensation is completed, and then are temporarily collected in a storage tank 43, from which a stream of condensed vapour 77' is withdrawn, from which a reflux stream 36' of second distillation chamber 79''' is obtained, as well as a stream 33' that contains hydrocarbons lighter than Pseudocumene, which is extracted from apparatus 9.

Figure 10:
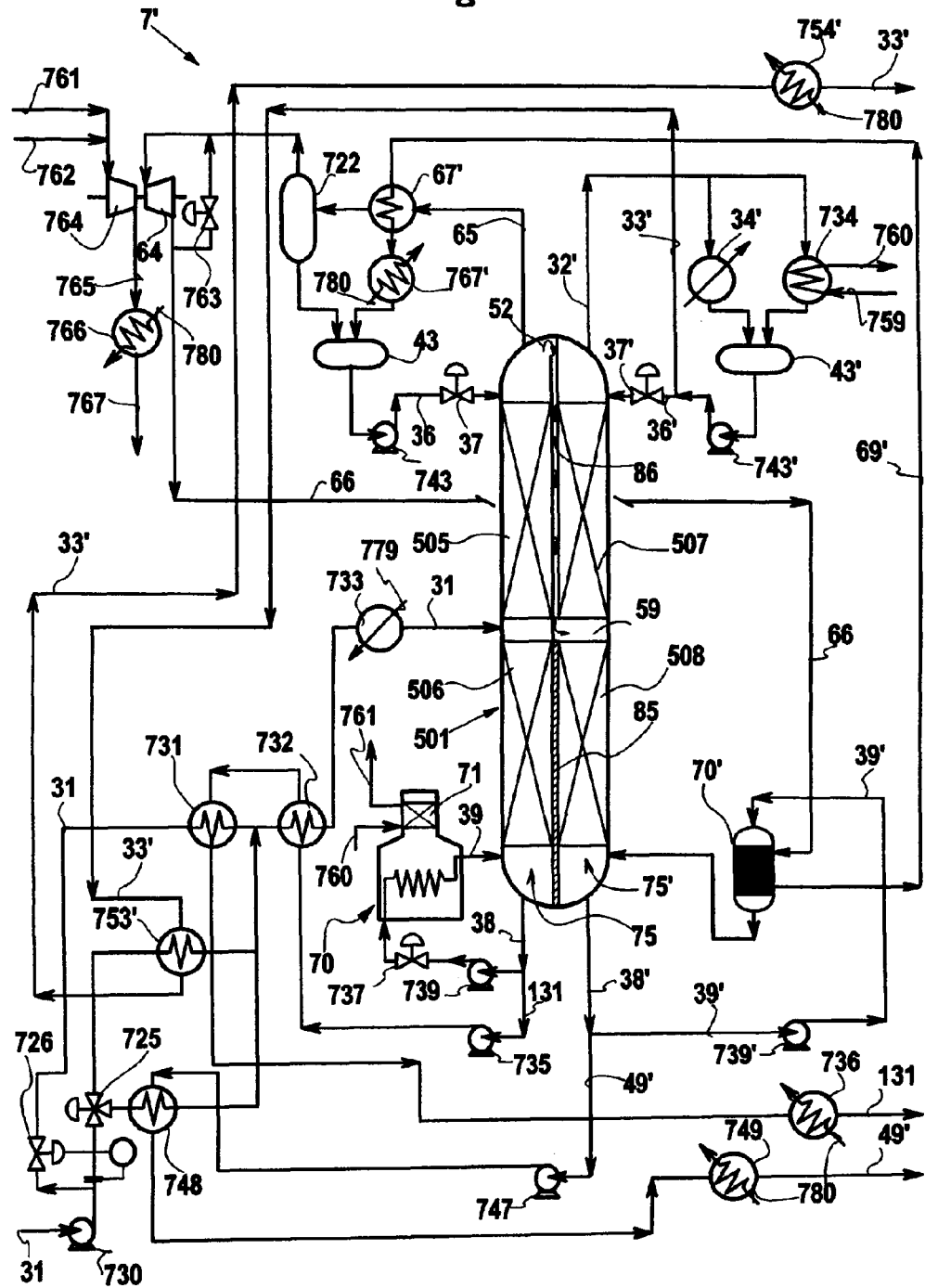
FIG. 10 is a flow diagram that shows a alternative way to recover energy from the overhead vapour that is extracted from the first chamber and from the second chamber.

FIG. 10 diagrammatically shows an apparatus 7' according to an exemplary embodiment of the invention, comprising a distillation column similar to column 501 of FIG. 5, for treating a raw mixture 31 that contains aromatic hydrocarbons with nine carbon atoms, and preferably hydrocarbons with more and/or less carbon atoms. An inner partition wall 85 defines two longitudinal chambers 75,75' in column 501, in each chamber two packings 505,506 and 507,508 are provided, which consist of low pressure-drop packing modules, typically Gauze® or Mellapack® type packings that are available from Sulzer. Apparatus 7' comprises heat exchangers 731,732,733,733',748 for pre-heating raw mixture 31, downstream of the pump of feeding 730. A stream of an overhead fraction 32 is partially condensed in an exchanger 67', and after flowing through a separation tank 722 for separating the liquid entrained in the vapour, is compressed by a condenser 64. Unlike apparatus 6 of FIG. 6, the condensation heat of compressed vapour 65 is used for reboiler 40' of second chamber 75' instead of for the reboiler of first chamber 75; in fact, the vapour that is extracted from first chamber 75 has an enthalpy difference with respect to bottom fraction 38' of second chamber 75' higher than the enthalpy difference with respect to bottom fraction 38 of first chamber 75, which makes thermocompression preferable to compressor 64. Once the condensation in reboiler 40' has been carried out, stream 69' of overhead fraction of the first column is (further) condensed in exchangers 67' and 767' forming, together with the liquid contained in the separator 722, reflux stream 36 of first chamber 75.

From a bottom section of first chamber 75, a liquid stream 38 of a bottom fraction is extracted, which contains hydrocarbons heavier than Pseudocumene. A first amount 39 of stream 38 is supplied by a pump 739 to the reboiler of the first chamber, at a flow rate controlled by a valve 737, consisting of a oven reboiler 70. A second amount 131 of stream 38, is withdrawn as the heavy product of fractionation unit 7' by a pump 735, and used for pre-heating feed raw mixture 31 in exchangers 732 and 731, and then that is further cooled in exchanger 736.

Oven reboiler 70 has a convective zone 71 in which low pressure saturated steam 760 is changed into low-pressure superheated vapour 761 and is used as motor fluid in a turbine 764 that operates compressor 64. The compression energy balance may also take into account a possible make-up 762 of steam coming from a steam generator external to apparatus 7'. The exhaust fluid 765 of turbine 764 is conventionally treated in a condenser 766 and/or in a steam trap 767.

Apparatus 7' comprises a column 501 in which the inner partition wall defines a channel 86 for feeding second chamber 75' with a stream 52 of the overhead vapour that is extracted from first chamber 75, which contains Pseudocumene and hydrocarbons that are lighter than Pseudocumene. However, the apparatus may also provide a column like column 301 of FIG. 3, in which second chamber 73' is fed by ducts external to column 301.

From a bottom section of second chamber 75' a liquid stream 38' of a bottom fraction is extracted, an amount 39' of which is treated in reboiler 40' that is associated with second chamber 73' and here recycled. A second amount 49' of stream 38' is withdrawn by means of a pump 747 as a substantially pure Pseudocumene product of fractionation unit 7', and is used for pre-heating feed raw mixture 31 in exchanger 748, and then is further cooled in exchanger 749.

A stream of a overhead vapour fraction 32', which contains aromatic hydrocarbons lighter than Pseudocumene, is extracted from distillation chamber 75', a part of it is condensed in a condenser 34', and another part of it is sent to a steam generator 734 to generate low-pressure steam 760 to be superheated in the convection zone 71 of oven reboiler 70. The condensate formed by the two parts is collected in a temporary storage tank 43', from which it is withdrawn by a pump 743' and is separated into a reflux stream 36', dosed to chamber 75' by a regulation valve 37', and into a stream 33' of hydrocarbons lighter than Pseudocumene, which is extracted from apparatus 7', after releasing a part of its own sensible heat to exchanger 753' for assisting a pre-heating of raw mixture feed 31, to be possibly further cooled in an exchanger 754'.

In apparatus 7', as shown in FIG. 10, the only external energy supply comes substantially from the fuel that is burnt in oven reboiler 70.

Figure 11:
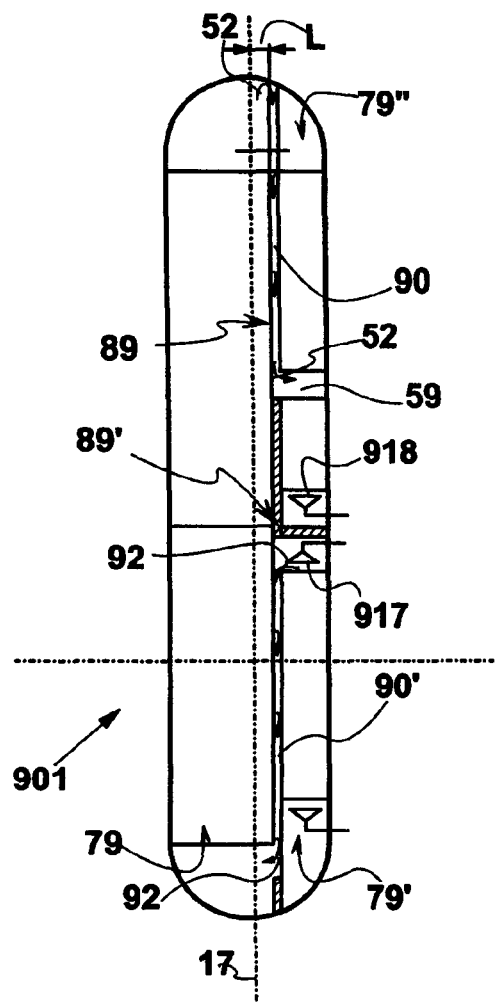
FIG. 11 shows an alternative exemplary embodiment of a distillation column that is equipped with an inner partition wall.
Figure 12A:
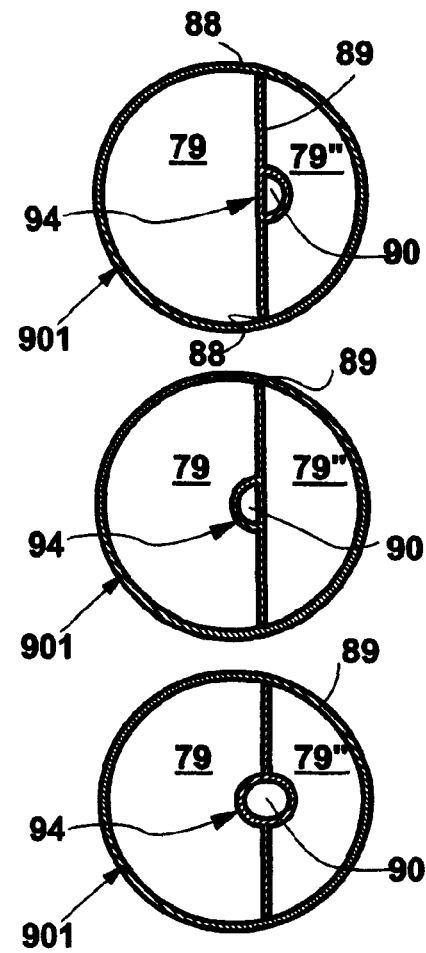

FIG. 11 shows an exemplary embodiment of a column of an apparatus according to the invention, in which inner partition wall 90 has portions that are arranged at a predetermined distance L from a diametrical plane 9 of the container of column 901, whereby, as show FIGS. 12A and 12B, the zones 931,932 of chamber 79 may have transverse sections 931',931' that have cross-sectional areas sensibly different from the cross-sectional area of transverse sections 932,933 and 934 of adjacent zones 932,933 and 934 of chambers 79' and 79".

As still shown in FIGS. 12A and 12B, passageway 90 may be defined in a zone of inner partition wall 89, that has a central position with respect to edges of conjunction 88 with the shell of container 901; more in particular, to adapt the cross sectional area to the flow rate of a stream of vapour such as streams 52,92 of FIGS. 5 and 9, inner partition wall 89 may have an enlarged cross section 94 at passageways 90,90', by making a protrusion of a portion of the cross section into at least one of chambers 79 and 79' or 79".

Figure 12C:
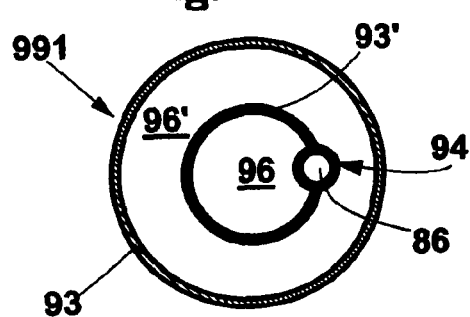
FIG. 12C shows a cross sectional view of an alternative exemplary embodiment of a distillation column equipped with an inner partition wall, in which the inner partition wall defines a longitudinal inner chamber and, together with the wall of the container, a longitudinal outer chamber.

As shown in FIG. 12C, an inner partition wall 93' of a distillation column 991, according to another exemplary embodiment, may have a closed cross section, in particular, a circular cross section; in this case, inner partition wall 93' defines a first longitudinal inner chamber 96, whereas a second longitudinal outer annular chamber 96' is defined between the outer wall 93 of the cylindrical container and inner partition wall 93'.

As shown in FIG. 13, an elongated container 951, which in the above described exemplary embodiments 301,501, 801,901 has the same cylindrical shape all along itself, i.e. it has only one diameter D, may also comprise more cylindrical portions, for example two coaxial cylindrical portions 97,97' that have different transverse sections, of respective diameters $D_1$ and $D_2$. Even if FIG. 13 shows a vertical exemplary embodiment 951 with cylindrical portion 97 of larger diameter $D_1$ arranged below a cylindrical portion 556 of smaller diameter $D_2$, in exemplary embodiments, not shown, that are adapted to specific working conditions is obviously possible, and it may be advantageous, to make a container with the larger diameter cylindrical portion arranged above the smaller diameter cylindrical portion.

The choice of a container having inner partition wall, according to one of the exemplary embodiments shown in FIGS. 11 and 13 may depend upon the composition of the raw mixture to be fractionated that is fed to the column, in particular, upon the concentration of aromatic hydrocarbons that are more/less lighter/heavier than Pseudocumene, vice-versa, as well as upon the conditions of the heating fluid/s that are available for reboiler 40,40',70,70', and upon still further conditions.

Figure 1A:
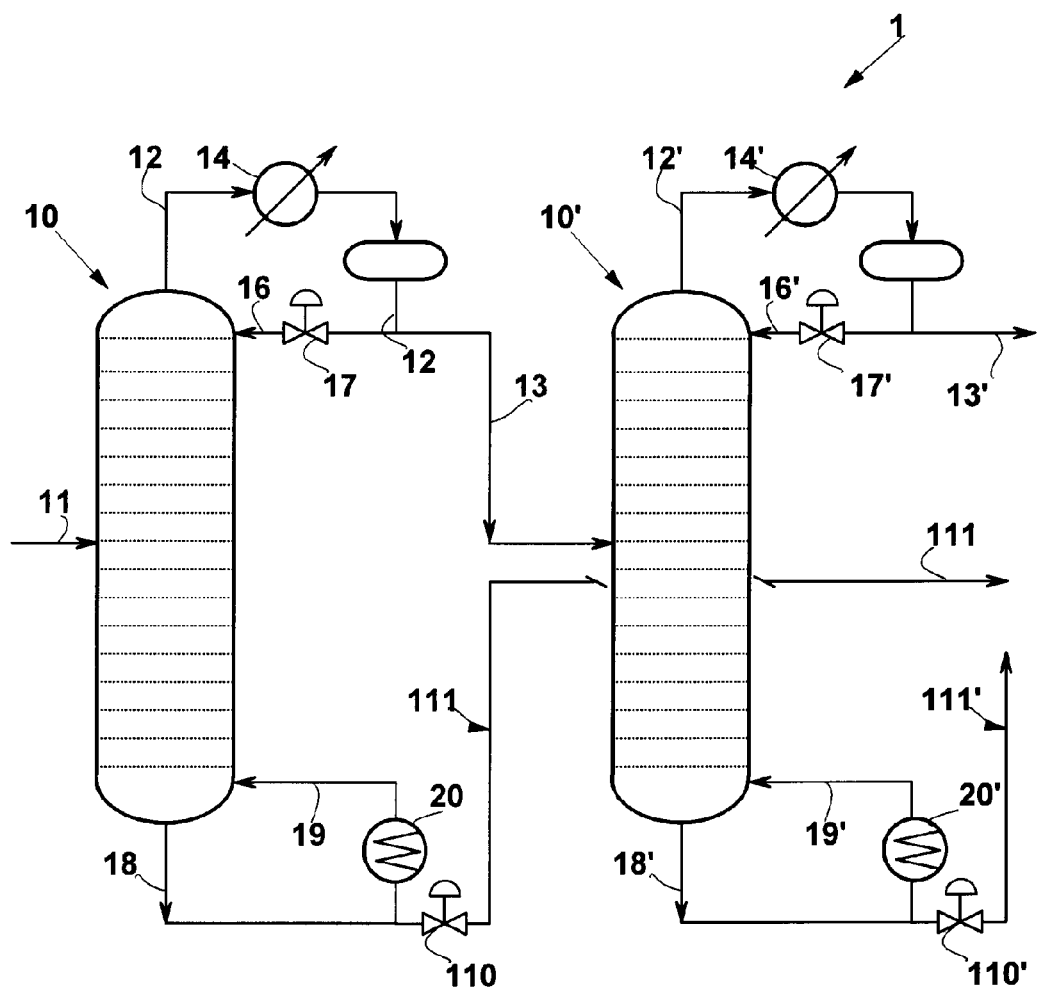
FIGS. 1A and 1B show process flow diagrams of known type for separating Pseudocumene from a C9 or C9+ aromatic hydrocarbon mixture according to the prior art.
Figure 1B:
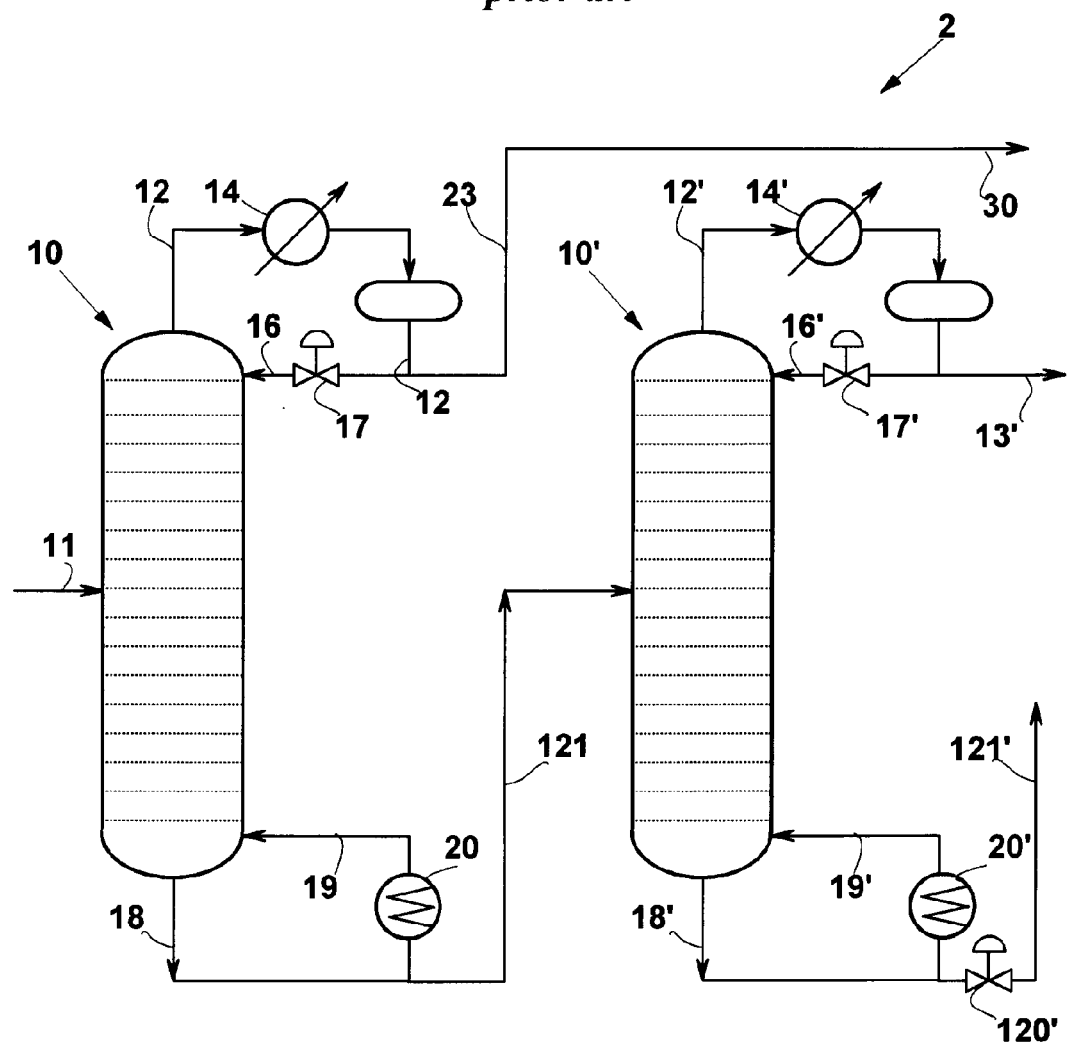
Figure 2B:
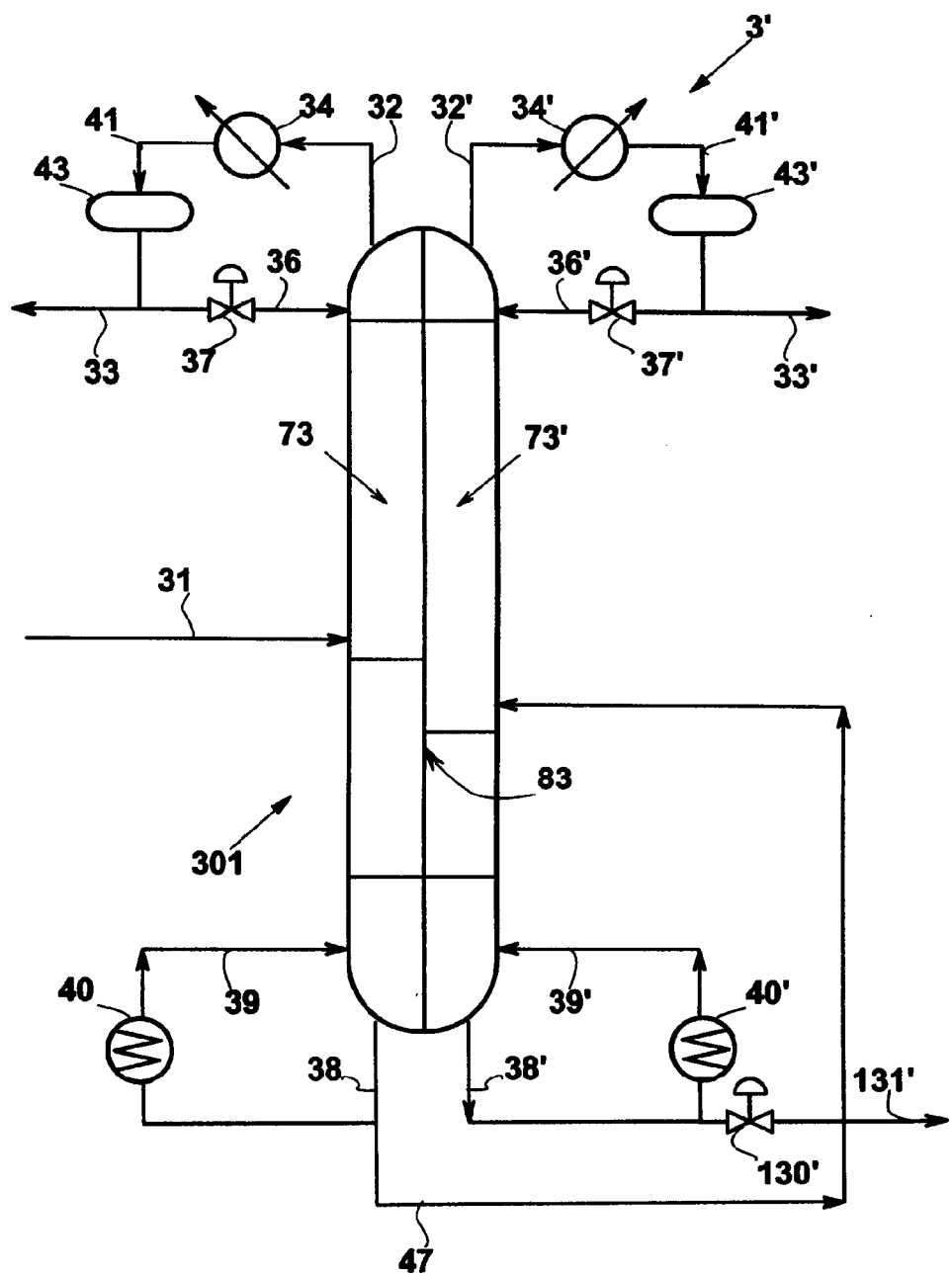
Figure 14:
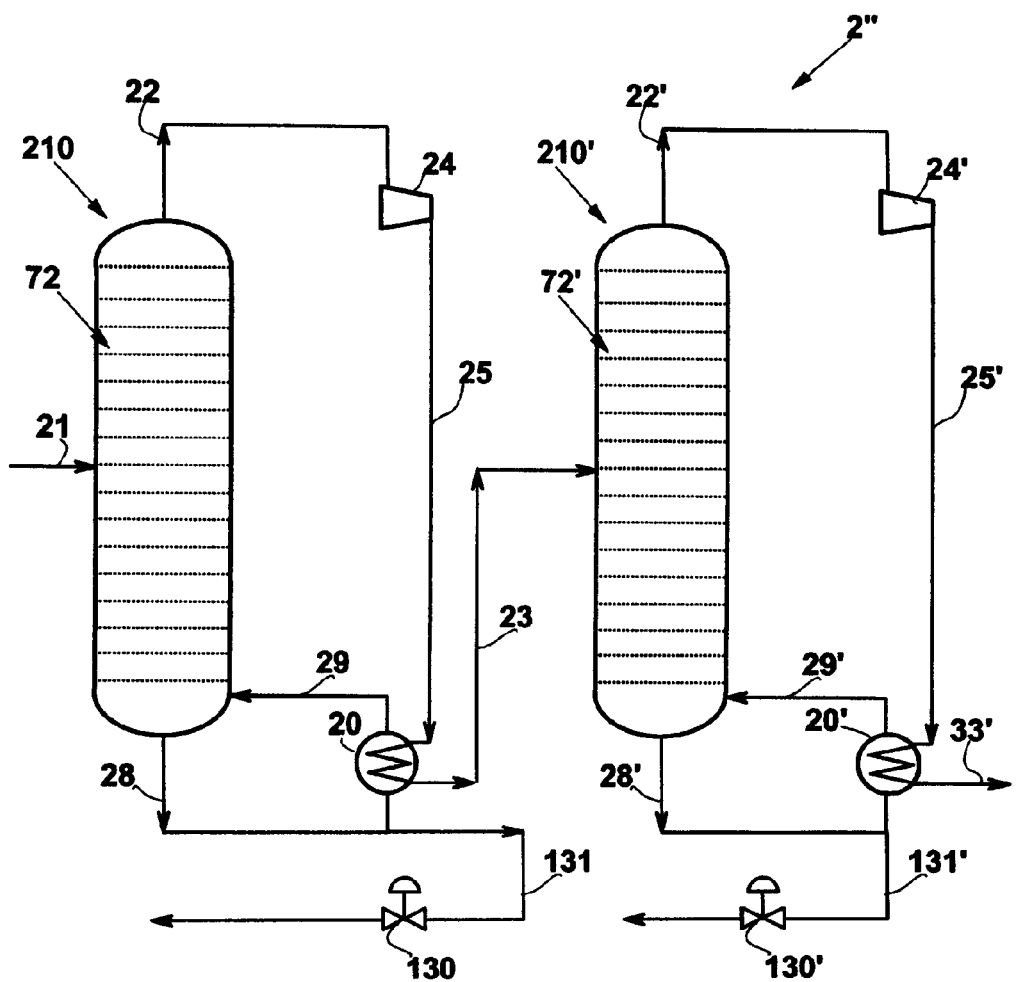
FIGS. 14 and 15 show process flow diagrams in which an amount of the overhead vapour that is extracted from each of a first distillation column and a distinct second distillation column undergoes a direct compression to allow a heat exchange for reboiling respective bottom fractions streams.
Figure 15:
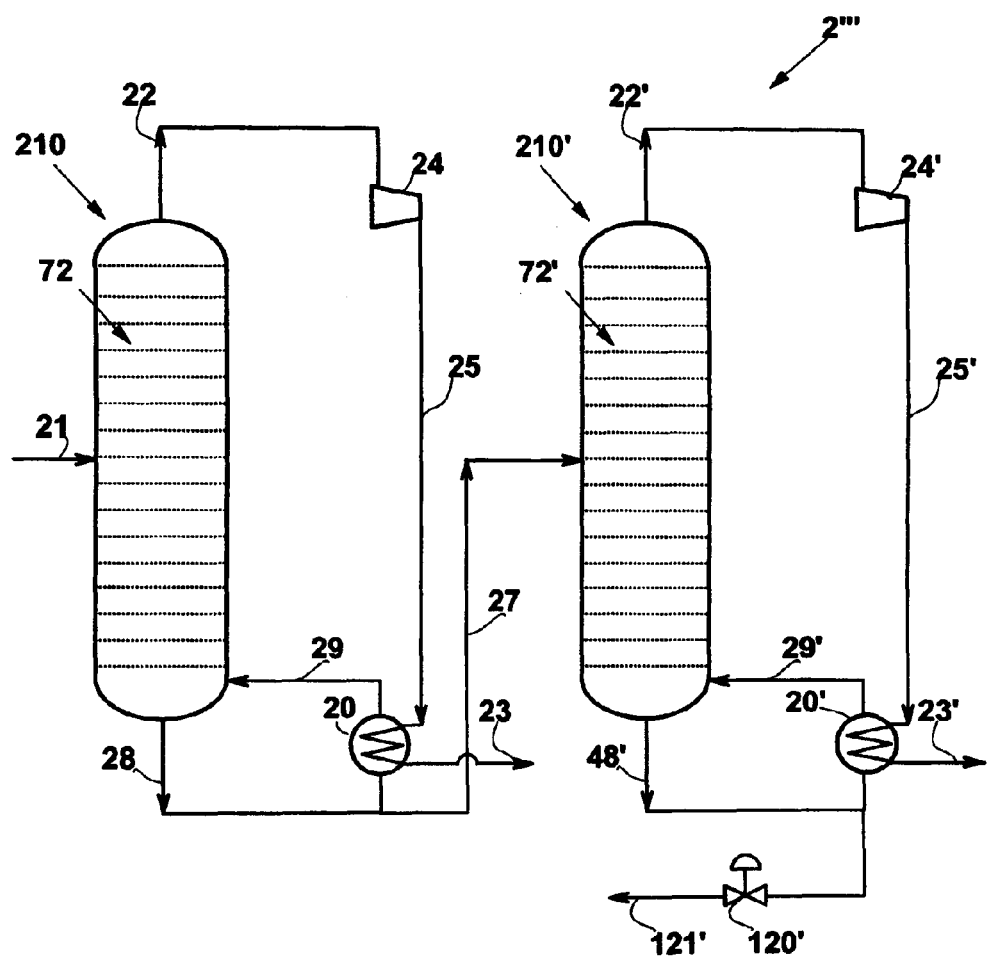

In FIGS. 14 and 15 two apparatuses 2",2''' are diagrammatically shown according to another aspect of the invention, which differ from apparatuses 1 and 2 of FIGS. 1 and 2 in that condensers 14,14' comprise two compressors 24,24', in particular, two one-stage compressors which are adapted to work at a compression ratio set between 1.5:1 and 5:1, and are used for compressing streams of overhead vapour 22,22'. Compressed vapour streams 25,25' are used in exchangers or reboiler 20,20' wherein, by an at least partial condensation, they release their own condensation heat respectively to streams 29 and 29' of bottom product;

FIGS. 16 and 17 diagrammatically show, respectively, two columns 310,320 for performing mass transfer operations between a first liquid or gas stream and a second liquid stream, according to two exemplary embodiments. Column 310 comprises a vertical container 311, in this case a cylindrical container, in which it a longitudinal dividing wall 385 is arranged that divides container 311 into a first longitudinal distillation chamber 375 and into a second longitudinal distillation chamber 376. Dividing wall 385 extends longitudinally, substantially vertically, between a lower end portion 318 and an upper end portion 319 of vertical container 311, in this case along axis 317 of the container 311.

Column 310 also comprises a feed means for feeding said first fluid stream 324 into said first chamber, an extraction means for extracting said first fluid stream 324 from said second chamber; a source 33 of said second stream, an extraction means 34 for extracting said second stream.

In the exemplary embodiment of FIG. 17, the column 320 comprises a container 311 in which it a longitudinal dividing wall 385 is arranged, which divides the container 311 into a first longitudinal distillation chamber 375 and into a longitudinal compartment 379. A transverse dividing wall 389 that divides longitudinal compartment 379 into a second longitudinal distillation chamber 376 and into a third longitudinal distillation chamber 377. Independently from transverse dividing wall 389, longitudinal dividing wall 385 of column 320 is arranged at a distance L from axis 317 of column 320, instead of at the axis, as in the case of column 310 of FIG. 16. Therefore, first distillation chamber 375 and compartment 379 are not symmetrical, nor are the respective transverse sections. For the sake of simplicity, the feed means is omitted in FIG. 17, as well as the means for extracting streams 324 and 325.

Columns 310 and 320 comprise inner passageways 386, 390 between one distillation chamber and the other. In particular, column 310 (FIG. 16) has a passageway 386 between an upper portion of first distillation chamber 375 and a central portion of second distillation chamber 376. Inner passageway 386 is arranged in a proximity, i.e. in a zone 315 adjacent to dividing wall 385. As shown in the cross sectional view of FIG. 18, proximity 315 comprises dividing wall 385 and the space directly adjacent to it.

More in detail, FIG. 16 diagrammatically shows a passageway 386 of column 310 that extends between an outlet port 312 of first distillation chamber 375 and an inlet port 313 of second distillation chamber 376. passageway 386 is adapted to convey a first process stream 324 from outlet port 312 of first distillation chamber 375 to inlet port 313 of second distillation chamber 376.

In FIG. 17, passageways 386,390 are arranged in the longitudinal dividing wall 385.

As diagrammatically shows FIG. 19, a column 330 according to an alternative exemplary embodiment comprises a passageway 386 that is located in a direct audiacence 315 (FIG. 18) of dividing wall 385, out of dividing wall 385. As shows FIG. 20, passageway 386 may consist of even more than one duct, for example it may consist of two tubes 391. Such duct or ducts 391 may be supported by dividing wall 385 itself, using a conventional fixing means, not shown. For simplicity, in FIG. 17 the feed means and the extraction means for streams 324 and 325 are also omitted.

Still with reference to FIG. 17, column 320 (FIG. 17) is also equipped with a further passageway 390 between an upper portion of third distillation chamber 375" and a lower portion of first distillation chamber 375. Inner passageways 385,390 of column 320 are shown in FIG. 17 as passageways inside longitudinal dividing wall 385, and may have any forms as described hereinafter for passageway 385 of column 310. Passageway 390 may be used for conveying a process stream, in particular, first stream 324, from third distillation chamber 377 to first distillation chamber 375.

exchange chambers 375,376,377 of exchange columns 310,320,330 may comprise a contact means between the first fluid phase and the second fluid phase, not shown. Such contact means may comprise any suitable conventional contact means, for example it may comprise mass transfer trays, and/or packings and/or structured packed beds.

As show still FIGS. 16,17,19, a phase-separation means 340 is also provided. Phase-separation means 340 are arranged along passageway 386, in other words, they are hydraulically/pneumatically connected with passageway 386. Therefore, they are enabled to receive first stream 324 that flows along the passageway.

In the present case of consecutive distillation steps, which are carried out in respective exchange chambers 375,376, first stream 324 is a gas stream that, when flows along passageway 385, contains a predetermined amount of liquid. In this case, phase-separation means 340 is adapted to at least partially remove the amount of liquid, forming a substantially gaseous main portion 327 and a secondary portion 327' (FIG. 22) of first, substantially liquid stream 324.

In the case of the distillation, first stream 324 may comprise the overhead vapour coming from first distillation chamber 375, which partially condensate along passageway 386, forming an amount of liquid. The condensation can occur, for example, if the two fractionation chambers operate at sensibly different temperatures, with respect to each other.

In summary, phase-separation means 340 allow to remove the amount of liquid or of a second liquid phase from first stream 324, upstream of or at most at inlet port 313 in the second distillation chamber 376.

As shown in FIGS. 16,17,19, the separation means 340 also comprises a feed means 348 of main portion 327 of first stream 324 at a predetermined feed height of second distillation chamber 376. As described hereinafter, secondary portion 327', containing the portion of liquid separated from the phase-separation means 340, may be recycled to the process, for example at a different feed height of the second exchange chamber, typically into a distillation column.

With reference to FIG. 21, a mass transfer column 360 is described, according to an exemplary embodiment of the invention, in which the phase-separation means 340 has a feed and distribution means 347,348 (see also FIG. 25) of main portion 327 and of secondary portion 327' of first stream 324. Feed means 347,348 allow to feed the first portion and the second portion at different feed heights of second distillation chamber 376, or in different exchange columns.

With reference to FIGS. 22,23 and 24 a phase-separation means 340 according to an exemplary embodiment is described more in detail. Such exemplary embodiment is adapted to a mass transfer column of inner diameter larger than 31 meter, and/or equipped with more than 320 trays, in particular, more than 330 trays.

Phase-separation means 340 comprise a decantation chamber 340' made along passageway 386, i.e. hydraulically and pneumatically connected with passageway 386. In the case shown, decantation chamber 340' is made within dividing wall 385.

Decantation chamber 340' has an inlet port 341 that is in communication with passageway 386, and is adapted to receive first stream 324, which comprises a first fluid phase and a second fluid phase. Therefore, decantation chamber 340' is equipped with outlet flow sections 343,343' of a lighter fluid phase, which may comprise a gas or a liquid. Flow sections 343,343' are pneumatically or hydraulically connected with feed/distribution means 348. Decantation chamber 340' is also equipped with outlet flow sections 344,344' for the heavier fluid phase, which may be a liquid, or a heavier liquid, separated from stream 324 as received by the decantation chamber 340'. Flow sections 343,343' are pneumatically or hydraulically connected with feed/distribution means 348. Flow section 343' minimum size is such that the passage speed of the gas portion is lower than a predetermined maximum value.

Decantation chamber 340' has a size large enough to allow stream 324 to split into a liquid portion and a gas portion. In particular, in the decantation chamber 340' a liquid head 342 is formed, or a head of a heavier liquid phase. Decantation chamber 340' has preferably a height H at least equal to two theoretical stages of second distillation chamber 376. In particular, height H of decantation chamber 340' is larger than 31000 mm, more in particular, it is larger than 31200 mm. The length L of decantation chamber 340' is preferably higher than or is about 31/3 of the inner diameter of the column. The width W of decantation chamber 340, defined perpendicularly to length L, is preferably greater than or equal to twice the equivalent diameter of outlet port 343', as above-defined.

Figure 25:
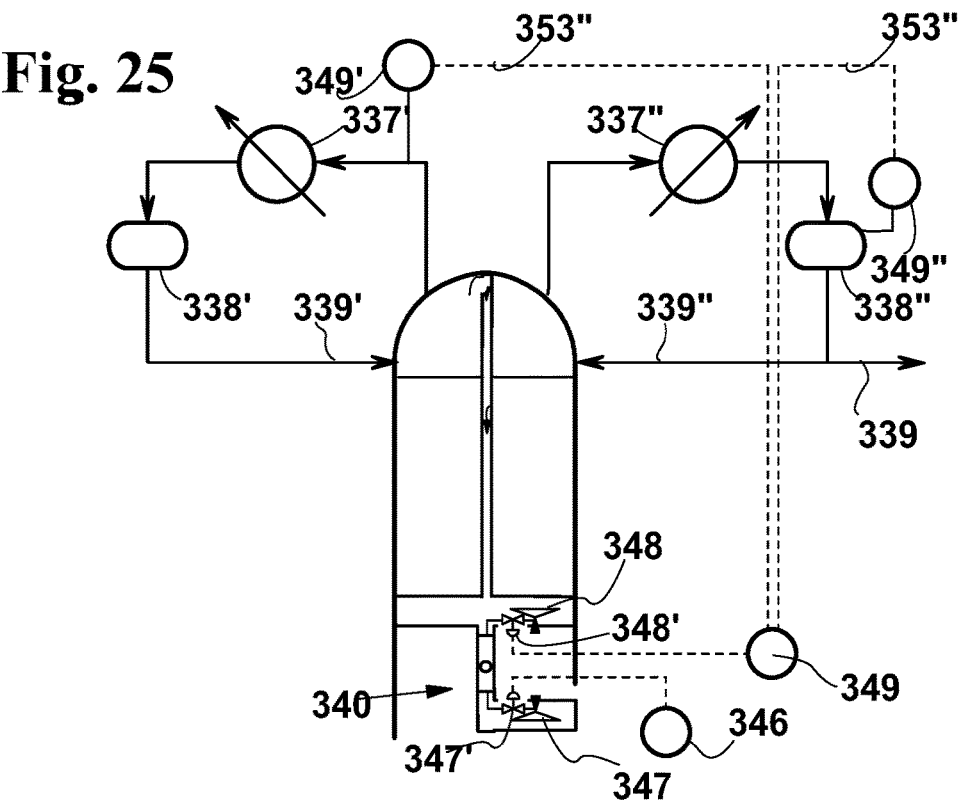
FIG. 25 is a process flow diagrams of the phase-separation means of FIGS. 7 and 8 in the case of a distillation column according to an exemplary embodiment of the invention.

In the exemplary embodiment of FIG. 22 and of FIG. 25, the decantation chamber has level connections 345 for measuring the level of head 342 by a level sensor. The level sensor is associated with a logical flowrate control unit 346 for the liquid that is fed into the lower distillation chamber or section 377. Flowrate logical control unit 346 is operatively connected with the regulation means of the flowrate, in particular, with a regulation valve 347'. Flowrate sensor and level connections 345 may be of known type.

Figure 26:
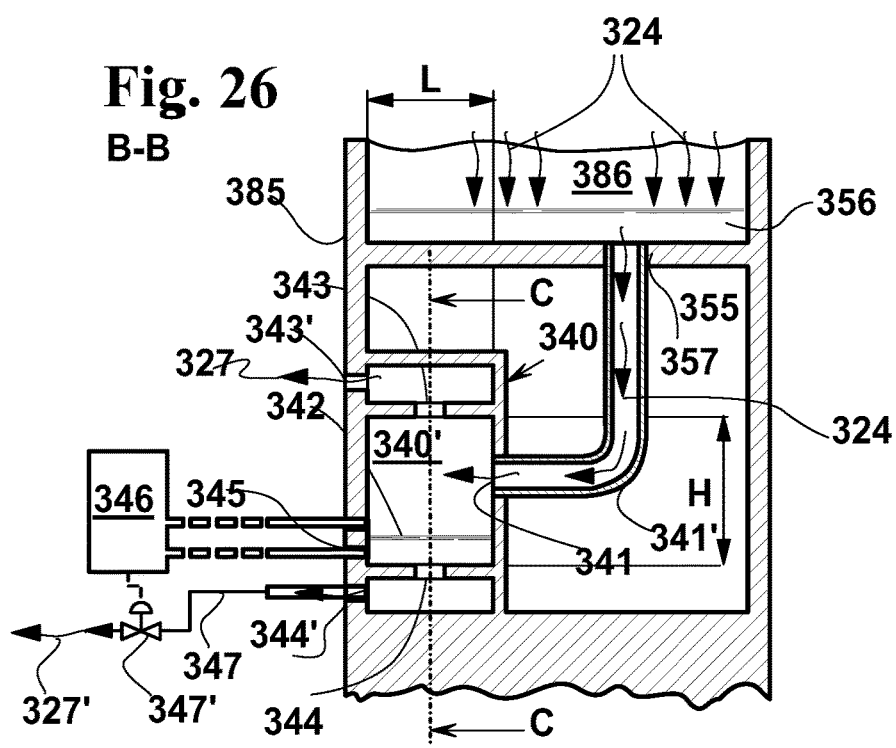
FIG. 26 is a diagrammatical longitudinal sectional view of the phase-separation means according to another exemplary embodiment.

In the exemplary embodiment of FIG. 25, a regulation device is diagrammatically shown for the flowrate of the vapour that is fed to second distillation chamber 376 of distillation chamber 360. The regulation device comprises two pressure sensors 349' and 349" that are associated with respective pressure transmitters to generate respective pressure signals 353',353" of the overhead vapour coming from said first distillation chamber 375 and from said second distillation chamber 376. The regulation device comprises also comparison and regulation logical means 349 that is adapted to receive pressure signals 353',353" and to generate a control signal for operating regulation element 348'. In an exemplary embodiment of FIG. 25, the regulation element comprises a regulation valve 348' that is arranged along feed and distribution means 348 of the vapour portion of first stream 324, as this is separated by phase-separation means 340, in order to operate regulation means 348' according to the pressure difference between the overhead vapour of first distillation chamber 375 and of second distillation chamber 376;

FIG. 26 shows an exemplary embodiment of separation means 340 of FIG. 22, where a collection tray 355 is provided in passageway 386 on which a liquid head 356 is formed. A hole is made through collection tray 355 for the liquid mixture-gas collected on tray 355. The hole 357 is connected to inlet port 341 by a duct 341' of suitable size.

In column 310 of FIG. 16, inlet port 313 of second distillation chamber 376 is arranged in a cross section which is located at an intermediate height between a bottom section of second distillation chamber 376 proximate to lower end portion 318, and a top section of second distillation chamber 376 proximate to upper end portion 319. For example, inlet port 313 is arranged at a feed section distillation chamber 376, which is provided with distillation means. Outlet port 312 of first distillation chamber 375 is made in the top section of column 310, in particular, outlet port 312 is an outlet port made at a zone where overhead vapour of distillation chamber 312 are present. The column of FIG. 1 is therefore adapted to recover a component of a multicomponent mixture by two consecutive distillation steps. In first distillation chamber 375 the heaviest components are removed from the component to be separated, and the top product contains the product to be separated along with lighter components. Top product 324 is fed to second distillation chamber 376, for example in vapour phase. In second distillation chamber 376 the lightest components are removed as the top product and the component to be separated is withdrawn as the bottom product.

The foregoing description of an embodiment of the method and of the apparatus according to the invention, and of the way of using the apparatus, will so fully reveal the invention according to the conceptual point of view, so that others, by applying current knowledge, will be able to modify and/or adapt for various applications such embodiment without further research and without parting from the invention, and, then it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology the is employed herein is for the purpose of description and not of limitation.

The invention claimed is:

1. An apparatus for separating and recovering Pseudocumene from a raw mixture containing aromatic hydrocarbons with nine carbon atoms, said apparatus comprising:
   a first chamber and a second chamber, said first chamber adapted to receive said raw mixture;
   a first feed means for feeding said first chamber with said raw mixture;
   a first top extraction means for extracting a first overhead vapour fraction from said first chamber;
   a first bottom extraction means for extracting a first bottom fraction from said first chamber;
   a second feed means for feeding said second chamber with a stream selected between a portion of said first overhead vapour fraction and a portion of said first bottom fraction;
   a second top extraction means for extracting a second overhead vapour fraction from said second chamber;
   a second bottom extraction means for extracting a second bottom fraction from said second chamber;
   a maintenance means for maintaining said first chamber and said second chamber within predetermined working temperature ranges and at predetermined respective operating pressures;
   wherein said maintenance means is adapted to maintain working temperature range and/or operating pressures such that:
   said Pseudocumene is present substantially in only one fraction selected between said first overhead fraction and said first bottom fraction, and
   a substantially pure Pseudocumene is contained only in one fraction selected between said second overhead fraction and said second bottom fraction, according to whether said Pseudocumene-containing fraction that is extracted from said first longitudinal chamber is said first bottom fraction or said first overhead fraction, respectively,
   wherein said apparatus comprises an elongated container that is adapted to be arranged vertically,
   an inner longitudinal partition wall arranged within said elongated container, said inner longitudinal partition wall defining said first chamber and said second chamber within said elongated container,
   a differential expansion compensation means arranged between said elongated container and said inner partition wall for compensating differential expansion due to a temperature difference between said first chamber and said second chamber,
   wherein said partition wall is internally fixed to a shell of said vertical elongated container at a short edge portion extension of said partition wall, and
   wherein other edge portions of said partition wall are arranged to have a relative freedom of movement with respect to said shell, and to allow an expansion of said partition wall with respect to said shell.

2. The apparatus according to claim 1, wherein said inner longitudinal partition wall has an inner passageway, said passageway extending between a top section of said first chamber and a feed section of said second chamber,
   said passageway being adapted to convey a stream of vapour from said first chamber to said second chamber, or from said second chamber to said first chamber.

3. The apparatus according to claim 1, wherein
   a transverse inner partition wall is provided within said container, which defines, along with said inner longitudinal partition wall, said first longitudinal chamber and said second longitudinal chamber, such that a continuation portion of said first longitudinal chamber is arranged on the same side of said second longitudinal chamber with respect to said inner longitudinal partition wall, and such that said inner longitudinal partition wall fluidically separates said continuation portion of said first chamber from a main portion of said first chamber;
   said first bottom extraction means is arranged on said continuation portion of said first chamber;
   said main part of said first chamber comprises a bottom feed means;
   said container also comprises:
   a top feed means for feeding a liquid stream into an upper portion of said third chamber;
   a third top extraction means for extracting a third overhead vapour fraction from said third chamber;
   a third bottom extraction means for extracting a third bottom fraction from said third chamber;
   and wherein
   a pneumatic connection is provided of said top feed means of said continuation portion of said first chamber with said first extraction means of said first chamber, and
   said third top extraction means is pneumatically connected with said bottom feed means of said main part of said first chamber, in order to provide a continuous fractionation path of said stream of vapour between said main part and said continuation portion of said first chamber, at opposite sides of said inner longitudinal partition wall.

4. The apparatus according to claim 3, wherein said second chamber and said continuation portion together comprise a number of separation stages that is substantially the same as the number of stages of said main part of said first chamber.

5. The apparatus according to claim 3, wherein said pneumatic connection comprises a further passageway that is defined within said inner longitudinal partition wall between said top feed means of said continuation portion of said first chamber and said first extraction means of said first chamber.

6. The apparatus according to claim 1, comprising:
a compression means for compressing at least one portion of said first overhead vapour fraction and/or at least one portion of said second overhead vapour fraction, said compression means adapted to provide a compressed overhead vapour at a compressed vapour pressure, such that said compressed overhead vapour has at least one of a condensation temperature that exceeds a boiling temperature of said first bottom fraction, and a condensation temperature that exceeds a boiling temperature of said second bottom fraction;
an indirect heat exchange means between said compressed overhead vapour and at least one part of said first bottom fraction and/or at least one part of said second bottom fraction, said heat exchange means adapted to cause a boiling of said at least one part of said first bottom fraction and/or a boiling of said at least one part of said second bottom fraction.

7. The apparatus according to claim 6, wherein said compression means can be operated by an expansion means for expanding an aeriform substance, and said apparatus comprises a means for generating said aeriform substance.

8. The apparatus according to claim 7, wherein said means for generating an aeriform substance comprises a steam generator that is associated with a heating means of said first bottom fraction and/or of said second bottom fraction.

9. The apparatus according to claim 6, wherein said first chamber and/or said second chamber comprises a fractionation means selected from the group consisting of:
distillation trays;
a packed bed; and
a combination thereof.

10. The apparatus according to claim 6, wherein a part of said fractionation means corresponding to a real fractionation stage is adapted to cause, in an operating condition of said first chamber and of said second chamber, a pressure drop lower than 20 millibar.

11. The apparatus according to claim 1, wherein said first chamber comprises a catalytic fractionation means that is arranged at a height above a feed port of said first longitudinal chamber, said catalytic fractionation means adapted to promote an alkylation reaction of said aromatic hydrocarbons with olefins that are contained in said raw mixture, bringing said olefins from a feed concentration to a residual concentration that is lower than 4 ppm, starting from a feed concentration that is normally set between 100 ppm and 300 ppm.

12. The apparatus according to claim 11, wherein said catalytic fractionation means comprises a catalytic material in the form of a packing material, said catalytic material selected from the group consisting of:
acid earths;
zeolites; and
a combination thereof.

13. The apparatus according to claim 11, wherein said maintenance means for maintaining said first chamber within a predetermined temperature range is adapted to maintain said catalytic fractionation means at an alkylation temperature set between 160° C. and 190° C.

14. The apparatus according to claim 12, wherein said packing material comprises a catalytic material having a height such that the spatial speed of the liquid phase of the mixture being distilled is set between 1.0 $h^{-1}$ and 10 $h^{-1}$.

15. The apparatus according to claim 1, wherein said first chamber and said second chamber are made within a column of exchange comprising:
a vertical elongated container that has a longitudinal dividing wall within said container, said container defining, with said dividing wall, said first chamber and said second chamber;
a means for feeding said raw mixture into said first chamber;
a means for extracting a first fluid stream from said second chamber;
a source of a second stream;
a means for extracting said second stream,
a contact means for causing a contact between said first stream and said second stream, said contact means arranged within said first chamber and/or within said second chamber;
a longitudinal passageway that extends between an outlet port of said first chamber and an inlet port of said second chamber, said passageway made in a proximity of said dividing wall for conveying said first stream from said first chamber into said second chamber;
wherein said contact means and/or said passageway are such that, in said passageway, said first stream comprises an amount of a substance in said second fluid phase,
wherein, along said passageway, a phase separation means that is adapted to receive said first stream and to form a main portion of said first stream and a secondary portion of said first stream, said secondary portion comprising at least a part of said amount of substance in said second fluid phase;
a feed means of said main portion of said first stream at a predetermined feed height of said second chamber, in order to remove said amount of substance in said second fluid phase from said first stream upstream of, or, at most, at said inlet port of said second chamber.

16. The apparatus according to claim 15, wherein said phase separation means comprises a means for feeding said secondary portion of said first stream to a further predetermined feed height of said second chamber.

17. The apparatus according to claim 15, wherein said phase separation means comprises a decantation chamber made within said passageway.

18. The apparatus according to claim 17, wherein said decantation chamber has a height greater than, or equal to, twice the height of a theoretical separation stage of said second chamber.

19. The apparatus according to claim 17, wherein said decantation chamber has a height higher or identical to 1000 mm.

20. The apparatus according to claim 17, wherein said decantation chamber has a transverse dimension that is higher, or about ⅓ of an equivalent inner diameter of said column.

21. The apparatus according to claim 17, wherein said decantation chamber has a second transverse dimension, defined perpendicularly to said first transverse dimension, and that is greater than, or equal to, twice an equivalent diameter of an outlet port of said main portion of said first stream.

22. The apparatus according to claim 17, wherein the decantation chamber has a connection means for a level sensor for measuring a level formed by said amount of substance in said second fluid phase within said decantation chamber.

23. The apparatus according to claim 4, wherein said second chamber and said continuation portion, on the one hand, and said main part, on the other hand, comprise the same number of trays, or substantially the same packed bed height.

* * * * *